United States Patent [19]

Iwasa et al.

[11] Patent Number: 5,142,026

[45] Date of Patent: Aug. 25, 1992

[54] RECOMBINANT HUMAN LYMPHOTOXINS THAT POSSESS N-TERMINAL EXTENDED LINKER PEPTIDES FOR ANTIBODY-BINDING SITES

[75] Inventors: Susumu Iwasa, Kyoto; Hiroko Tada, Hyogo, both of Japan

[73] Assignee: Takeda Chemical Industries, Ltd., Osaka, Japan

[21] Appl. No.: 346,745

[22] Filed: May 3, 1989

Related U.S. Application Data

[63] Continuation-in-part of Ser. No. 330,298, Mar. 29, 1989, abandoned.

[30] Foreign Application Priority Data

Apr. 7, 1988 [JP] Japan .................................. 63-83972

[51] Int. Cl.$^5$ ............................................. C07K 13/00
[52] U.S. Cl. ..................... 530/351; 530/395; 530/820; 530/402
[58] Field of Search .............. 530/351, 395, 820; 435/69.1, 69.5

[56] References Cited

U.S. PATENT DOCUMENTS

| | | | |
|---|---|---|---|
| 4,677,063 | 6/1987 | Mark et al. | 530/351 |
| 4,677,064 | 6/1987 | Mark et al. | 530/351 |
| 4,752,525 | 6/1988 | Granger et al. | 530/351 |
| 4,920,196 | 4/1990 | Aggarwal | 424/85.1 |

FOREIGN PATENT DOCUMENTS

| | | |
|---|---|---|
| 0175617 | 9/1985 | European Pat. Off. |
| 0232107 | 1/1987 | European Pat. Off. |
| 025000 | 6/1987 | European Pat. Off. |
| 0208615 | 7/1987 | European Pat. Off. |
| 0272894 | 12/1987 | European Pat. Off. |

OTHER PUBLICATIONS

Pennicor et al, Nature Mar. 2, 1984, pp. 724–729.
CA vol. 108, #92969x, Kakutani et al.
Bringman et al., Hybridoma, 6, 489 (1987).
Gray et al., Nature, 312, 721 (1984).
Tada et al., Journal of Immunoassay, 10, 93 (1989).
Tada et al., Hybrodoma, 8, 73 (1989).
Tada et al., The Physico-chemical Biology, 33, 39 (1989).

Primary Examiner—Garnette D. Draper
Attorney, Agent, or Firm—David G. Conlin; Ernest V. Linek

[57] ABSTRACT

Disclosed is a novel recombinant human lyphotoxin (LT) mutein which combines with an antibody at an inactive site of an LT molecule and liberates the LT molecule easily from the antibody after incorporation of the mutein into tumor cells.

The recombinant human LT mutein is prepared by introducing a polydeoxyribonucleic acid containing a nucleotide sequence coding for the particular amino acid sequence into a replicable vector, transforming a microorganism or a cell with the recombinant DNA thus obtained, and cultivating the resulting transformant to express genetic information of the polydeoxyribonucleic acid.

The recombinant human LT mutein is useful for tumor-selective carcinostatics, and effective for increasing the activly of LT and reducing the side effects thereof.

1 Claim, 6 Drawing Sheets

FIG. 6

```
                                          28          30
             (Met) |Lys Ser Ala Leu Ala Leu Ser Asp| Lys Pro Ala Ala His Leu Ile Gly Asp Pro Ser Lys Gln Asn Ser Leu
GAATTCT ATG        AAG TCT GCG CTA GCG CTG TCT GAC  AAG CCA GCT GCT CAC CTC ATT GGA GAC CCC AGC AAG CAG AAC TCA CTG
EcoRI              NheI Eco47III                                    PvuII                        40
                                                                                                      pTB1004
```

FIG. 7

```
                                          28          30
             (Met) |Cys Ser Ala Leu Ala Leu Ser Asp| Lys Pro Ala Ala His Leu Ile Gly Asp Pro Ser Lys Gln Asn Ser Leu
GAATTCT ATG        TGT TCT GCT CTA GCG CTG TCT GAC  AAG CCA GCT GCT CAC CTC ATT GGA GAC CCC AGC AAG CAG AAC TCA CTG
EcoRI                   Eco47III                                    PvuII                        40
                                                                                                      pTB1005
```

FIG. 8

```
                                      27                30
             (Met) |Cys Ser Gly Phe Leu Gly Ser| Leu Lys Pro Ala Ala His Leu Ile Gly Asp Pro Ser Lys Gln Asn Ser Leu
GAATTCT ATG        TGC TCC GGA TTT CTC GGA TCT  CTC AAG CCA GCT GCT CAC CTC ATT GGA GAC CCC AGC AAG CAG AAC TCA CTG
EcoRI              AccIII                                           PvuII                        40
                                                                                                      pTB1006
```

FIG. 9

```
                                                10
             (Met) |Cys Ser Gly Phe Leu Gly Ser Leu Lys Pro| Ala Ala Gln Thr Ala Arg Gln His Pro Lys Met His
GAATTCT ATG        TGC TCC GGA TTT CTC GGA TCT CTC AAG CCA  GCT GCT CAG ACT GCT AGA CAG CAT CCT AAG ATG CAT
EcoRI              AccIII                                   PvuII                              20
                                                                                                  pTB1007
```

RECOMBINANT HUMAN LYMPHOTOXINS THAT POSSESS N-TERMINAL EXTENDED LINKER PEPTIDES FOR ANTIBODY-BINDING SITES

CROSS REFERENCE TO RELATED APPLICATION

The present invention is a continuation-in-part of copending application Ser. No. 07/330,298, filed Mar. 29, 1989, abandoned, the disclosure of which is hereby incorporated herein by reference.

BACKGROUND OF THE INVENTION

This invention relates to a novel bioactive polypeptide useful as a carcinostatic and a polydeoxyribonucleic acid (hereinafter referred to as DNA) having genetic information thereof.

This invention also relates to a replicable recombinant DNA containing the above DNA and a microorganism or a cell transformed with the replicable recombinant DNA, and further relates to the novel bioactive polypeptide obtained by expression of the DNA's genetic information and a process for producing the same.

Lymphotoxin (hereinafter referred to as LT) is a protein having antitumor activity derived from lymphocytes, which is expected to have clinical application in a manner similar to tumor necrosis factor (hereinafter referred to as TNF) derived from macrophages. These proteins, LT and TNF have been obtained by adding an endotoxin or a phorbol ester to lymphocytes or macrophages, respectively, for activation thereof. However, with the progress of gene manipulation techniques, the structures of these proteins have recently become identified. As a result, it has become possible to produce these proteins by cultivation of microorganisms or cells using the genes coding for these proteins. Gray et al. [*Nature*, 312, 721 (1984)] and Pennica et al. [*Nature*, 312, 724 (1984)] each succeeded in cloning them using the gene manipulation techniques.

On the other hand, through advances in gene techniques, the mass-production of LT and TNF has recently become possible so that their clinical trials can be conducted. However, the results of clinical tests, particularly the clinical data of TNF, are not necessarily satisfactory [T. Taguchi *Cancer and Chemotherapy*, 13, 3491 (1986), I. Urushizaki, *Oncologia*, 20, 105 (1987) and A. Klansne, *Biotech.*, 5, 335 (1987)]. The most serious problem encountered is the appearance of strong side effects. The administration of TNF is accompanied by fervescence, ague, trepidatio, depression of blood pressure and the like. Therefore, TNF has a disadvantage that the growth of tumors can not be prevented due to the necessity of the interruption of its administration. In addition, the tumor selectivity of TNF is not as good as was first thought. It has been found that normal cells and fibroblasts also have TNF receptors [Y. Niitsu, *Therapeu. Res.*, 7, 275 (1987)], and normal cells which react with TNF have also been discovered.

The clinical results with respect to LT are not as plentiful as those about TNF. However, from the fact that LT has a structure very similar to that of TNF and has the property of combining with common receptors on cells [B. Y. Rubin, et al. *J. Exp. Med.*, 162, 1099 (1985)], it is presumed that the nonspecific cytotoxicity to non-tumor organs, tissues and cells will likewise appear and side effects similar to those of TNF will be induced.

Thus, conventional TNF and LT present a complicated clinical picture. Therefore the application of novel preparations, including new modifications and combination therapy are desired.

On the other hand, as drugs for killing tumor cells selectively, antitumor immune conjugates, each of which is prepared by combining an anti-cancer antibody with a chemotherapeutics or a biotic toxin, have been developed. These have a characteristic of recognizing tumor-specific antigens or tumor-associated antigens on tumor cells, combining therewith and terminating the DNA synthesis or the protein synthesis of the tumor cells to kill them. Therefore, these drugs are specific against tumor organs, tissues and cells, and have little side effect to normal cells. Some antibody-medicament or antibody-biotic toxin conjugates have already been submitted to clinical applications, and several good results have been obtained.

In order to enhance the tumor specificity of LT which is a human-derived toxin having strong cytotoxic activity, the present inventors have studies to obtain a novel immunotoxin combined with an antitumor antibody, under the technical background described above. In the preparation of such an immunotoxin, two important problems ave ben considered. One is that the conventional LT or LT mutein has the high possibility of combining with an antibody at an active site on the molecule and the biological activity of LT itself is impaired in the course of the above combining. The other is that the expression of the activity of LT si presumed to be very little, because the toxin portion, namely the LT molecule, is not liberated from the antibody after incorporation of LT into tumor cells and accordingly difficult to transfer to a target site in the cells, even if the immunotoxin is synthesized somewhat maintaining the biological activity of LT.

In this specification, amino acids and peptides are indicated by the abbreviations adopted by IUPAC-IUB Committee of Biochemistry Nomenclature (CBN). For example, the following abbreviations are used:
Gln: Glutamine residue
Asp: Asparatic acid residue
Pro: Proline residue
Tyr: Tyrosine residue
Val: Valine residue
Lys: Lysine residue
Glu: Glutamic acid residue
Ala: Alanine residue
Asn: Asparagine residue
Leu: Leucine residue
Phe: Phenylalanine residue
Gly: Glycine residue
His: Histidine residue
Ser: Serine residue
Thr: Threon
Ile: Isoleucine residue
Trp: Tryptophan residue
Arg: Arginine residue
Met: Methionine residue
Cys: Cystine residue When the optical isomer is capable of existing with respect to the amino acids and the like, the L-form is represented unless otherwise specified.

Also in this specification, polymers or oligomers of DNA are indicated by the sequence of the following abbreviations:

A: 2'-Deoxyadenylic acid residue
C: 2'-Deoxycytidylic acid residue
G: 2'-Deoxyguanylic acid residue
T: Thymidylic acid residue Unless otherwise stated, the direction from the left to the right in sequence indicates the direction from the 5'-position to the 3'-position.

BRIEF DESCRIPTION OF THE DRAWINGS

The abbreviations and their meanings in each drawing are as follows:
B: Bal I
Ba: BamH I
Bg : Bgl II
C : Cla I
E : EcoR I
H : Hind III
N : Nsi I
P or Ps : Pst I
Pu : Pvu II
S : Sal I
X : Xho I
B I : Bgl I
E 47 : Eco 47 III FIGS. 5 to 9 show the 5'-terminal DNA sequences coding for human LT muteins, which are contained in plasmids pTB953, pTB1004, pTB1005, pTB1006 and pTB1007, respectively, and amino acid sequences deduced therefrom.

DISCLOSURE OF THE INVENTION

Figure 1:
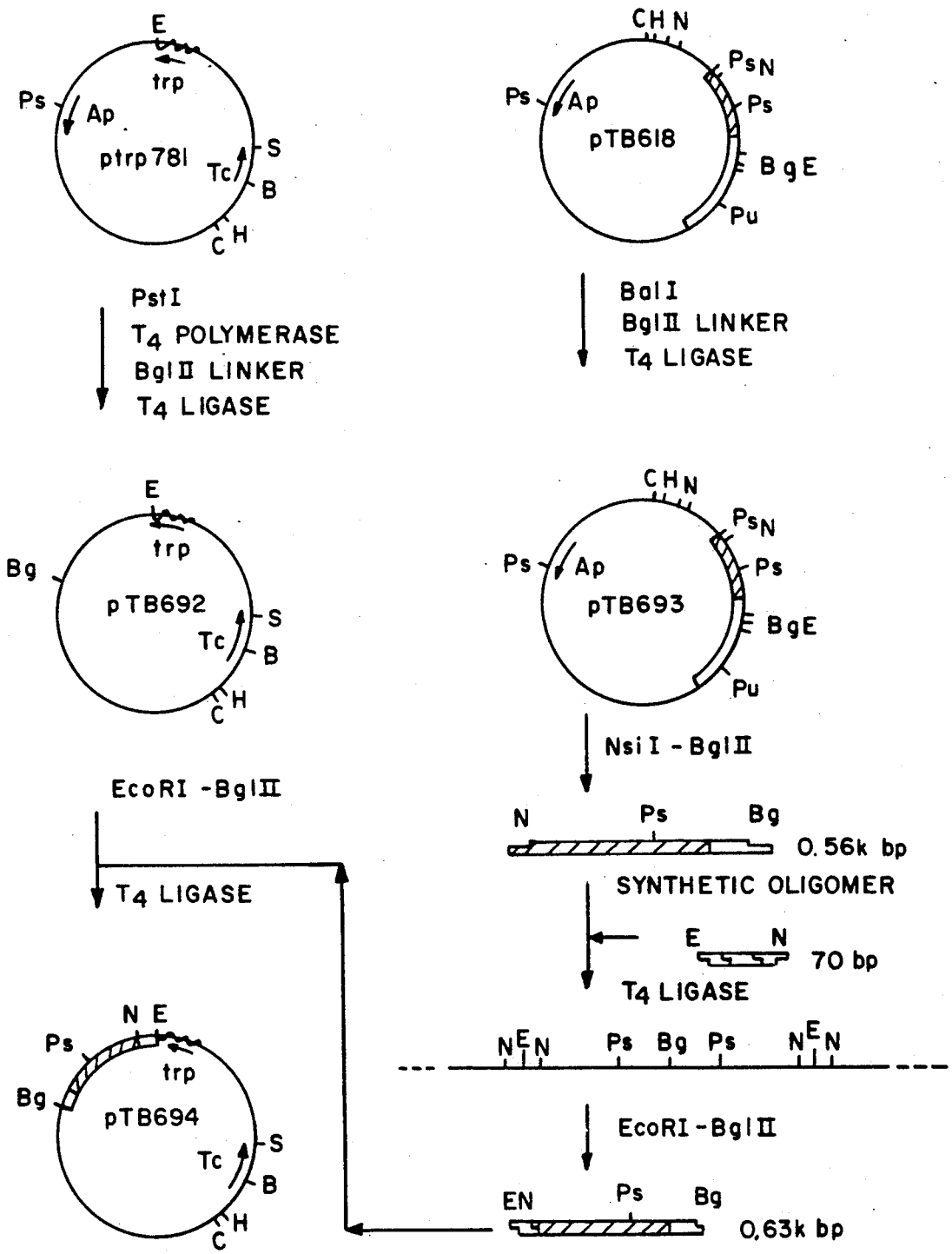
FIGS. 1 to 4 are schematic representations which show the construction of recombinant plasmids pTB694, pTB773, pTB858 and pTB864.

It is therefore a primary object of the present invention to provide a novel recombinant human LT mutein which combines with an antibody at an inactive site of a LT molecule and liberates the LT molecule easily from the antibody after incorporation of the mutein into tumor cells.

Other objects of this invention will be apparent from the following description and the accompanying drawings.

In accordance with the present invention, there is provided a protein comprising the following amino acid sequence or a part of an active portion of said protein:
H-(mit)-N-$R_1$-$R_2$-($R_3$)-Lys-Pro-ala-Ala -His-Leu-Ile-Gly-Asp-Pro-Ser-Lys-Gln -Asn-Ser-Leu-Leu-Trp-Arg-Ala-Asn -Thr-Asp-Arg-Ala-Phe-Leu-Gln-Asp-Gly -Phe-Ser-Leu-Ser-Asn-Asn-Ser-Leu-Leu -Val-Pro-Thr-Ser-Gly-Ile-Tyr-Phe-Val-Tyr -Ser-Gln-Val-Val-Phe-Ser-Gly-Lys-Ala -Tyr-Ser-Pro-Lys-Ala-Thr-Ser-Ser-Pro -Leu-Tyr-Leu-Ala-His-Glu-Val-Gln-Leu-Phe -Ser-Ser-Gln-Tyr-Pro-Phe-His-Val-Pro -Leu-Leu-Ser-Ser-Gln-Lys-Met-Val -Tyr-Pro-Gly-Leu-Gln-Glu-Pro-Trp-Leu -His-Ser-Met-Tyr-His-Gly-Ala-Ala-Phe -Gln-Leu-Thr-Gln-Gly-Asp-Gln-Leu-Ser -Thr-His-Thr-Asp-Gly-Ile-Pro-His-Leu -Val-Leu-Ser-Pro-Ser-Thr-Val-Phe-Phe -Gly-Ala-Phe-Ala-Leu-OH
wherein $R_1$ is Cys, Lys, Ser, Cys-Ser or Lys-Ser, $R_2$ is Ala-Leu-Ala, Leu-Ala-Leu, Leu-Ala-Leu-Thr, Ala-Leu-Ala-Leu, Ala-Leu-Ala-Leu-Ser-Asp-Lys-Pro Ala-Leu-Ala-Leu-Ser -Asp, Gly-Phe-Leu-Gly-Ser, Gly-Phe-Leu-Gly-Ser-Leu -Lys-Pro or Gly-Phe-Leu-Gly, R is a peptide chain represented by Ala-Ala-Gln-Thr-Ala-Arg-Gln -His-Pro-Lys-Met-His-Leu-Ala-His-Ser-Thr-Leu or a part thereof, m is 0, and n is 0 or 1.

In the above sequence, $R_1$ is an amino acid residue or peptide chain having an antibody-combining functional group, $R_2$ is a lysosome-sensitive linker peptide chain, and $R_3$ is the N-terminal portion of N-terminal deleted LT, which is all or a part of amino acids situated in the 10th to 27th positions of LT represented by Ala10-Ala-Gln-Thr-Ala-Arg-Gln -His-Pro-Lys-Met20-His-Leu-Ala-His-Ser-Thr-Leu27.

Further, the present invention includes a polydeoxyribonucleic acid containing the nucleotide sequence coding for the polypeptide described above and a polydeoxyribonucleic acid containing the sequence complementary thereto.

The present invention relates to a replicable recombinant DNA which can express the polypeptide containing the amino acid sequence described above in a transformed microorganism or cell. Examples of such recombinant DNAs include pTB773, pTB775, pTB858, pTB860 and pTB864.

Furthermore, the present invention relates to a microorganism or a cell transformed by the replicable recombinant DNA capable of expressing the polypeptide shown by the amino acid sequence of LT described above. Such microorganisms or cells include, for example, *Escherichia coli, Bacillus subtilis,* yeast and higher animal cells.

Still furthermore, the present invention relates to a process for producing LT, which comprises expressing the gene coding for the novel LT mutein in a microorganism or cell. More particularly, it relates to a process for producing the polypeptide, which comprises cultivating the microorganism or cell transformed with the replicable recombinant DNA and recovering the peptide efficiently.

The DNA coding for the novel LT mutein of the present invention can be prepared, for example, by the following process:

1. m-RNA can be collected by methods known in the art from human peripheral blood lymphocytes in which the synthesis of LT is induced by 12-o-tetradecanoylphorbol-13-acetate (TPA) and concanavalin A (ConA). Further, about $5 \times 10^5$ cDNA library can be prepared therefrom.

2. An oligonucleotide from 10-mer to 50-mer coding for a partial peptide chain of LT is synthesized. By using this oligonucleotide as a probe, the screening of LT cDNA is conducted. For example, when a synthetic nucleotide of 18-mer (TCCAAAGAAGACAGTACT) at the C-terminal side is used, about 50 clones can be obtained.

3. Plasmids are isolated from the LT cDNA clones thus obtained and the nucleotide sequence is determined. A plasmid coding for the amino acid sequence of LT described above is selected, cleaved with an appropriate restriction enzyme, and then suitably inserted into an expression vector. Thus, recombinant DNA containing the DNA fragment can be prepared.

4. Various kinds of hosts, for example *Escherichia coli,* are transformed by using the vector prepared in item 3. Consequently, strains containing DNA coding for LT can be obtained.

5. After cultivating the transformants obtained in item 4 and isolating the plasmids, the DNA coding for the novel LT mutein is prepared as follows:

(1) In case of the human LT gene, the restriction enzyme Nsi I recognition site is located in the region coding for methionine-histidine situated in the 20th–21st positions from the N-terminus. Then, by digesting the LT gene with Nsi I at that site, the DNA fragment coding for N-terminal-deleted LT can be obtained. The DNA coding for the novel LT mutein is produced by combining an adapter containing the following sequence and DNA coding for the amino acid sequence containing an antibody-combining amino acid or peptide and a linker peptide with the above fragment, and the produced DNA fragment is inserted into an appropriate vector:

```
5'       3'
 GAATTCATG
 CTTAAGTAC
3'       5'
```

(2) Similarly, in the case of the human LT gene, the restriction enzyme Pvu II recognition site is located in the region coding for serine-alanine situated in the 9th–10th positions from the N-terminus. Then, by digesting the LT gene with Pvu II at that site, the DNA fragment coding for N-terminal deleted LT can be obtained. The DNA coding for the novel LT mutein is produced by combining an adapter containing the sequence shown in item (1) and DNA coding for the amino acid sequence containing an antibody-combining amino acid or peptide and a linker peptide with the above fragment, and the produced DNA fragment is inserted into an appropriate vector.

(3) After the cleavage with Pvu II or Nsi I, the DNA fragment coding for N-terminal-deleted LT is further treated with an exonuclease such as nuclease BAL31 to remove the region coding for 1–18 amino acid residues therefrom, with which an adapter containing the sequence shown in item (1) and DNA coding for the amino acid sequence containing an antibody-combining amino acid or peptide and a linker peptide are combined. Then, by selecting the DNA fragment in which the reading frame of the gene is correctly maintained, the DNA fragment coding for the novel LT mutein in which an antibody-combining amino acid or peptide and a linker peptide are combined to the N-terminal portion of LT (x−171), x=10–20, can be prepared.

(4) The technique of a site-directed mutagenesis (M. Smith and S. Gillam, *Genetic Engineering,* 3. 1 (1981) may also be applied. Namely, after the cleavage with Pvu II, the DNA fragment coding for N-terminal deleted-LT is inserted into vector M13, with which *Escherichia coli* JM103 (Pharmacia P-L Biochemicals) is infected. After cultivation, M13 phages released in the broth are precipitated with polyethylene glycol and treated with phenol, whereby single-stranded M13 phage DNA can be obtained.

Then, there is prepared by chemical synthesis methods the DNA coding for a polypeptide chain in which an amino acid or peptide of a part of the peptide chain from alanine situated in the 10th position to leucine situated in the 27th position from the N-terminus of LT is cleaved and an antibody-combining amino acid or peptide and a linker peptide are combined to the N-terminal portion thereof. The polypeptide thus prepared can be used as a primer. This primer is mixed with the M13 phage DNA fragment previously prepared to form a double-stranded DNA by DNA polymerase I large fragment. Thereafter, the cyclization thereof can be achieved by T4 DNA ligase. The circular DNA thus obtained is inserted into *Escherichia coli* JM103 and the released M13 phage DNAs are transferred to a filter. Then, by using the synthesized primer labeled with $^{32}P$, plaque hybridization [T. Maniatis, et al., *Molecular Cloning, A Laboratory Manual,* Cold Spring Harbor Labornatory, p.312 (1982)]is carried out. A DNA is prepared from the phage from which a strong signal is detected, and cut out with an appropriate restriction enzyme. The DNA fragment thus obtained is introduced in a plasmid to provide a DNA fragment coding for the modified novel LT mutein.

Plasmid DNA, cosmid DNA, phage DNA and the like containing the whole or a part of the human LT gene can be used as a template DNA for the site-directed mutagenesis. M13 phage or $\phi$X174 phage is desirable as a template DNA, because a single-stranded DNA can be easily prepared therefrom. For example, when M13 phage or $\phi$X174 phage in which the whole or a part of the human LT gene is introduced is used, the phage particles which are present in the broth are precipitated with polyethylene glycol, deproteinized by phenol treatment, and then precipitated with ethanol, to obtain a single-stranded DNA in the phage particle. When a double-stranded plasmid DNA or cosmid DNA in which the whole or a part of the human LT gene is introduced is used as a template DNA, a double-stranded DNA is subjected to heat treatment at 100° C. for 1 to 10 minutes, preferably 3 to 5 minutes, and then cooled rapidly with ice water to be denatured to a single-stranded DNA, prior to the use.

The primer for the site-directed mutagenesis may have any DNA sequence, so long as it has a DNA sequence to which the sequence shall be changed, and functions as the primer on the DNA synthesis through hybridization with a templete DNA. Also, the primer may be produced by any method, but it is desirable to prepare a single-stranded DNA having an appropriate sequence by chemical synthesis method. Such a primer is mixed with the single-stranded DNA previously prepared, and repaired to a double-stranded DNA by DNA polymerase I large fragment. Thereafter, the cyclization can be achieved by T4 DNA ligase. After the circular DNA thus obtained is introduced into *Escherichia coli,* plaque hybridization [T. Maniatis, et al., *Molecular Cloning, A Laboratory Manual,* Cold Spring Harbor Laboratory, p.312 (1982)] or colony hybridization (ibid. p.326) is carried out, using the primer labeled with a radioisotope as a probe, whereby the desired mutant can be selected. By using phage DNA or plasmid DNA prepared from the plaque or the colony thus obtained, the novel LT mutein gene can be prepared.

The recombinant DNA capable of expressing the DNA coding for the novel LT mutein can be constructed, by inserting the DNA fragment coding for the novel LT mutein thus obtained at the 3'-terminus of the promoter region which functions in various hosts such as *Escherichia coli, Bacillus subtilis,* yeast and cells.

Any promoter region is available, if the region contains a site necessary for initiating the mRNA synthesis by the linkage of RNA polymerase.

For example, when *Escherichia coli* is used as a host, the recombinant DNA capable of expressing DNA coding for the novel LT mutein can be constructed by inserting the DNA fragment coding for the novel LT mutein at the 3'-terminus of the promoter region capable of functioning in *Escherichia coli.* When the host is Escherichia coli, there is used pBR322, pBR325, ptrp781, pUC8, pUC9, pUC19, pJB8 or the like as the vector, and the DNA fragment coding for the novel LT mutein is inserted therein by T4 DNA ligase. By using this restriction solution, *Escherichia coli* such as C600 strain, MM294 strain, DH1 strain, W3110 strain, PR1 strain, PR13 strain or the like is transformed according to the known method [S. N. Cohen, et al., *Proc. Natl. Acad. Sci. U.S.A.*, 69, 2110 (1972)] or a method similar thereto.

The promoter used need not be limited to the trp promoter (trp-p). For example, there may be used a recA promoter (Japanese Patent Unexamined Publication No. 59-65099), a lac promoter, a $\lambda P_L$ promoter or the like.

The transformant carrying the novel recombinant plasmid DNA containing the DNA fragment coding for the novel LT mutein obtained as described above can be selected as a phenotype, for example, an ampicillin resistance type, a tetracycline resistance type or a resistance type to these drugs.

The transformant described above is cultivated in any of media known in the art. Such media include, for example, L-broth, Penassay broth and M-9 medium containing glucose and Casamino Acid (J. Miller, *Experiments in Molecular Genetics*, 431–433, Cold Spring Harbor Laboratory, New York, 1972). In order to allow the promoter to act efficiently, a drug such as 3$\beta$-indolylacrylic acid may be added thereto if necessary.

The cultivation of the transformant is generally carried out at 15° to 43° C., preferably 28° to 40° C. for 2 to 24 hours, preferably 4 to 16 hours, with aeration or agitation if necessary.

For example, when an animal cell is used as the host, the DNA fragment coding for the novel LT mutein is inserted at the 3'-terminus of the region of the promoter (such as SV promoter) capable of functioning in the animal cell. The host is transformed with the recombinant DNA by methods known in the art, and then the transformant is cultivated, whereby the novel LT mutein can be produced.

When *Bacillus subtilis* or yeast is used as the host, the DNA fragment coding for the novel LT mutein is inserted at the 3'-terminus of the region of the promoter capable of functioning in *Bacillus subtilis* or yeast. The host is transformed with the recombinant DNA by methods known in the art, and then the transformant is cultivated, whereby the novel LT mutein can be produced.

Of the hosts described above, *Escherichia coli* is more preferable.

After cultivation, the cells are collected by methods known in the art. In case of the transformant of *Escherichia coli*, the cells are suspended in an appropriate buffer solution, for example, Tris-hydrochloric acid buffer (pH 7.5) and disrupted by ultrasonic treatment, lysozyme and/or freeze-thawing. Thereafter, the supernatant containing the novel LT mutein is obtained by centrifugation. Preferably, there can be employed a method in which the collected cells are suspended in a buffer solution, to which lysozyme is added, then incubated at 0 to 10° C. for 10 minutes to 3 hours, and thereafter treated with ultrasonication at 0° to 10° C. for 30 seconds to 5 minutes, followed by centrifugation to obtain the supernatant.

The separation and purification of the novel LT mutein from the extract can be carried out by, for example, gel filtration, hydroxyapatite column chromatography, ion exchange column chromatography, ultracentrifugation and affinity chromatography using a human LT antibody.

As the amino acid or peptide having an antibody-combining functional group contained in the N-terminal portion of the novel LT mutein according to the present invention, there may be used Cys, Lys, Ser, Cys-Ser, Lys-Ser or the like. Each of Cys and Cys-Ser is combined with an antibody through a sulfhydryl group. Particularly, human LT can be very specifically combined with an antibody through the N-terminal portion of LT which is an inactive site, because Cys is not included in its molecule. Each of Lys and Lys-Ser can be combined with an antibody through $\alpha$- and $\epsilon$- amino acid groups included therein. Further, each of Ser, Cys-Ser and Lys-Ser can be combined with an antibody through a hydroxyl group included therein.

For combining an antibody with human LT, there are used various methods known in the art [V. P. Butler, *Pharmacol. Rev.*, 29, 103 (1978) and T. Kitagawa, *Organic Synthetic Chemistry*, 42, 283 (1984)]. For Example, the following methods are considered to be useful:

(1) An antitumor antibody modified with N-succinimidyl pyridyl dithiopropionate (hereinafter referred to as SPDP) is added to a LT mutein of the present invention containing Cys at the N-terminus thereof to prepare a conjugate by a thiol exchange reaction.

(2) An antitumor antibody maleimidated with N-(Y-maleimido butyryloxy)-succinimide (hereinafter referred to as GMBS) is added to a LT mutein of the present invention containing Cys at the N-terminus thereof to prepare a conjugate by thioether bonding.

(3) An LT mutein containing Lys at the N-terminus thereof which is modified with SPDP and then reduced is added to a maleimidated antitumor antibody modified with SPDP to prepare a conjugate by thioether bonding.

(4) Similarly, an LT mutein containing Lys at the N-terminus thereof which is modified with SPDP and then reduced is added to an antibody modified with SPDP to prepare a conjugate by a thiol exchange reaction.

In these methods, antibody fragment F(ab')$_2$, Fab' or Fab may be used in place of antitumor antibody IgG. Further, the antibody and the LT mutein can be substituted for each other in the treatment to prepare the conjugate.

Then, as the lysosome enzyme-sensitive linker peptides contained at the N-termini of the novel LT muteins of the present invention, there are used Ala-Leu-Ala, Leu-Ala-Leu, Leu-Ala-Leu-Thr, Ala-Leu-Ala-Leu, Ala-Leu-Ala-Leu-Ser-Asp-Lys-Pro, Gly-Phe-Leu-Gly and the like. Any peptide chains known in the art may be used if they are sensitive to lysosome enzymes. Particularly, the above-mentioned linkers containing Ala-Leu-Ala, Leu-Ala-Leu, Ala-Leu-Ala-Leu or Gly-Phe-Leu-Gly are preferably used, because liberation to medicament is effectively performed after their incorporation in a cell [B. Rihova et al., *Clin. Immunol. Immunopathol.*, 46, 100 (1988) and A. Trouet et al., *Proc. Natl. Acad. Sci. U.S.A.*, 79, 626 (1982)].

There are hereinbefore described the methods for producing the gene of the novel LT mutein and for producing the novel LT mutein by using the gene. However, the present invention is not limited thereto.

In the present invention, the whole or a part of the nucleotide sequence can be substituted with an artificial DNA fragment synthesized chemically, without changing the amino acid sequence, due to the known differences in usage frequency of codons(genetic code) corresponding to each amino acid.

The novel LT muteins of the present invention have an amino acid or a peptide which can be used for the bonding with an antibody, at the N-terminal portion not relating to their activity, and include a lysosome enzyme-sensitive linker peptide located next to that sequence. Therefore, immune conjugates can be formed without impairing the biological activity of LT itself on combining with an antitumor antibody. Moreover, it is expected that the LT molecule is liberated from the antibody by the influence of an intracellular lysosome enzyme to exhibit the effective cytotoxicity, after the incorporation into an antitumor cell. These characteristics are very advantageous for preparing tumor-selective carcinostatics, and effective for increasing the activity of LT and reducing side effects.

The present invention will hereinafter be described in detail with the following Reference Examples and Examples. It is understood, of course, that these example are not intended to limit the scope of the invention.

In carrying out the present invention, preparation of recombinant DNA and insertion of the recombinant into a microorganism were conducted according to the following experimental textbooks unless otherwise stated:

(1) T. Maniatis, E. F. Fritsch and J. Sambrook, *Molecular Cloning*, published by Cold Spring Harbor Laboratory (U.S.A.), (2) Edited by Y. Takagi, *Gene Manipulation Experimental Method*, published by Kodansha (Japan).

REFERENCE EXAMPLE 1

Evaluation of Cytotoxic Activity against L929 Cell

The cytotoxicity of LT was measured by the method corresponding to that described in *J Immunol.*, 126, 235 (1981) or *J. Immunol. Methods*, 70, 257 (1984), using L929 cells. Namely, 50 μl of L929 cells suspended at a concentration of $4 \times 10^5$ cells/ml in RPMI 1640 medium supplemented with 10% fetal calf serum (FCS) containing 4 μg/ml of mitomycin C were added to 50 μl of a sample stepwise, twice diluted with the above-mentioned medium by using a microplate for tissue cultivation (Flow Laboratory) having 96 wells, and then cultivated in 5% carbon dioxide gas at 37° C. for 48 hours. After completion of the cultivation, the live cells were dyed with dimethylthiazolyl diphenyltetrazolium bromide (MTT), and dissolved with 10% SDS-0.01N HCl. Thereafter, the optical density at 590 nm was measured with a Titertek Multiscan (Flow Laboratory). The optical density obtained is proportional to the number of live cells. The amount of biological activity required for killing 50% of L929 cells was defined as 1 unit/ml, and the biological activity of the sample was represented by unit/ml.

REFERENCE EXAMPLE 2

Preparation of *Escherichia coli* Strain for Transformation (1)

A colony of *Escherichia coli* DH1 strain was cultivated in SOB medium [see the experimental textbook (1), p. 69], until an optical density at 500 nm reached to 0.5. Then, 30 ml of the culture was collected and suspended in 12 ml of 0.2 M acetate buffer (pH 5.8) containing 0.1 M RbCl, 10 mM $CaCl_2$, 50 mM $MnCl_2$ and 15% glycerol. After cooling with ice for 5 minutes, the suspension was centrifuged. Then, the resulting mixture was resuspended in 10 mM MOPS buffer (pH 6.5) containing 10 mM RbCl, 75 mM $CaCl_2$ and 15% glycerol. The resulting suspension was cooled with ice for 15 minutes, then rapidly frozen with dry ice-ethanol, and thereafter stored at −70° C.

REFERENCE EXAMPLE 3

Preparation of *Escherichia coli* Strains for Transformation (2)

Colonies of *Escherichia coli* strains DH1, C600 and MM294 were cultivated in 10 ml of SOB medium until the optical density at 550 nm reached 0.3. After cooling with ice, the resulting cultures were centrifuged. The cells obtained were washed with 5 ml of 10 mM NaCl. The cells were resuspended in 5 ml of 50 mM $CaCl_2$ and allowed to stand for 15 minutes under ice cooling. After centrifugation, the cells were suspended in 0.5 ml of 50 mM $CaCl_2$ and used immediately thereafter.

EXAMPLE 1

Preparation of cDNA Library by Using mRNA Derived from Human Lymphocytes

The lymphocytes prepared from human peripheral blood were cultivated in RPMI 1640 medium (supplemented with 10% FCS) containing TPA (15 ng/ml) and ConA (40 μg/ml) at 37° C. to induce LT. After 24 hours, $1 \times 10^{10}$ cells of the induced human lymphocytes were disrupted for denaturation by a Teflon homogenizer in a solution containing 5 M guanidine thiocyanate, 5% mercaptoethanol, 50 mM Tris-HCl (pH 7.6) and 10 mM EDTA. Thereafter, sodium N-lauroyl sarcosinate was added thereto to a concentration of 4%, and the homogenized mixture was layered on 6 ml of 5.7 M cesium chloride solution (5.7 M cesium chloride and 0.1 M EDTA). The resulting mixture was centrifuged by a Beckmann SW 28 rotor at 24,000 r.p.m. at 15° C. for 48 hours, whereby the precipitate of RNA was obtained. After this precipitate of RNA was dissolved in 0.25% sodium N-lauroyl sarcosinate solution, precipitation with ethanol was carried out, whereby 10 mg of RNA was obtained. The RNA thus obtained was adsorbed on an oligo(dT) cellulose column in a high salt solution [0.5 M NaCl, 10mM Tris-HCl (pH 7.6), 1 mM EDTA and 0.3% SDS], and 300 μg of mRNA containing poly(A) was obtained by elution of mRNA containing poly(A) with a low salt solution [10 mM Tris-HCl (pH 7.6), 1 mM EDTA and 0.3% SDS].

The mRNA thus obtained was further precipitated with ethanol, and dissolved in 0.2 ml of a solution [10 mM Tris-HCl (pH 7.6), 2 mM EDTA and 0.3% SDS]. After treatment at 65° C. for 2 minutes, fractionation by 10–35% sucrose density gradient centrifugation (by a Beckmann SW28 rotor, at 25,000 r.p.m. at 20° C. for 21 hours) was conducted. For each of the fractions, a part of RNA was injected into oocyte cells of *Xenopus laevis* and the LT activity in protein to be synthesized was measured. As a result, the activity of LT was detected in the fraction corresponding to a sedimentation constant of about 16S. The amount of LT mRNA in this fraction was about 25 μg.

Using the poly(A) RNA as a template, a cDNA library was prepared by using pcDV1 vector and pL1 linker according to the method of Okayama and Berg [*Mol. Cell. Biol.*, 2, 161 (1982); *ibid.*, 3, 280 (1983)]. *Escherichia coli* DH1 was infected with circular vector plasmids containing cDNA, and a cDNA library of about $5 \times 10^5$ clones of which the host was *Escherichia coli* DH1 could be obtained from 5 μg of poly (A) RNA.

EXAMPLE 2

Isolation of Plasmid Containing Human LT cDNA and Determination of Nucleotide Sequence Thereof The above human cDNA library using *Escherichia coli* DH1 was inoculated to 10 nitrocellulose filters (Millipore, HATF filter) up to $3 \times 10^4$ clones/filter. Twenty (20) replica filters (each pair consisting of 2 filters) were prepared from the above 10 master filters. Plasmid DNA exposed for denaturation by lysing *Escherichia coli* on the replica filter with 0.5N NaOH solution was dried for fixation on the filter [M. Grunstein and D. S. Hogness, *Proc. Natl. Acad. Sci. U.S.A.*, 72, 3961 (1975)].

On the other hand, an oligonucleotide having the following formula, which corresponded to a portion (the gene portion corresponding to amino acid No. 162-167) of the nucleotide sequence of th LT gene already reported [Gray et al., *Nature*, 312, 721 (1984)], was synthesized and used as a screening probe for human LT cDNA:

The 5'-terminus of the oligonucleotide probe was labeled with $^{32}P$ by using T4polynucleotide kinase and [$\gamma$-$^{32}P$]ATP.

The labeled probe was hybridized with each of the replica filters on which DNA was fixed. The hybridization reaction was carried out at 40° C. for 16 hours in 10 ml of a solution of $5 \times SSC$ (0.15 M NaCl, 0.015 M sodium citrate), 5 ×Denhardt's, 0.1% SDS and 100 $\mu$g/ml of denatured salmon sperm DNA, containing 10 $\mu$Ci of the labeled probe. After completion of the reaction, the filters were washed with a solution of $6 \times SSC$ and 0.1% SDS at room temperature for 30 minutes 3 times and further at 43° C. for 60 minutes twice [the experiment textbook (1), p. 309]. Radioautograms were taken from the washed filters and the radioautograms of the replica filters in sets of two filters were put together in layers for searching the cells reactive to the probe. By this method, 50 strains of *Escherichia coli* DH1 reactive to the probe were obtained from about $3 \times 10^5$ colonies.

The plasmid DNA was extracted and purified from these cells by the alkaline method [H. C. Birnboim and J. Doly, *Nucleic Acids Res.*, 7, 1513 (1979)]. The DNA was cleaved by the restriction enzyme BamH I (Takara Syuzo) and fractionated by agarose gel electrophoresis. Thereafter, the DNA fragments were transferred on a nitrocellulose filter (BA85 manufactured by S & S) [Southern blotting method, the experimental textbook (1), p. 382]. When this filter was hybridized with the oligonucleotide probe described above, the plasmid DNA fragments reacted with the probe.

Then, one strain of *Escherichia coli* K12 DH1/pTB618 having the plasmid which had the largest BamHI DNA fragments (cDNA portions) among others was selected. The nucleotide sequence of the cDNA portion of this plasmid DNA was determined by the dideoxynucleotide synthetic chain termination method [J. Messing et al., *Nucleic Acids Res.*, 9, 309 (1981)].

As a result, it was proved that th LT gene contained in plasmid pTB618 was not complete and included from the non-translated portion on the 3'- terminal side upstream to the third C of codon CCC of Pro which was the 18th amino acid.

EXAMPLE 3

Construction of Human LT (1-171) Expression Vector pTB 694

Process 1 (Preparation of pTB693 Plasmid DNA)

As shown in FIG. 1, 2 $\mu$g of plasmid pTB618 was digested at 37° C. for 6 hours by using 0.6 unit of Bal I (Takara Syuzo).

On the other hand, 2 $\mu$g of a Bgl II linker of 8-mer represented by CAGATCTG was phosphorylated with 0.5 mM ATP and 2.5 units of T4 polynucleotide kinase. Then, 0.2 $\mu$g of the phosphorylated linker was added to 1.6 $\mu$g of Bal I-digested pTB618, and the mixture was reacted int he presence of T4 DNA ligase at 14° C. overnight. After inactivation at 65° C. for 5 minutes, the reaction product was trimmed by 30 units of Bgl II, and subjected to 1.2% agarose gel electrophoresis.

A main band corresponding to 4.3 Kbp was cut out, extracted with Tris-hydrochloric acid buffer, an then purified by an RDP minicolumn (Bio RAD). To 100 ng of the linear DNA fragment described above, 10 units of T4 DNA ligase was added to obtain DNA containing pTB693 plasmid, with which *Escherichia coli* DH1 strain was transformed according to methods known in the art. In detail, the DH1 cells for transformation prepared and stored in the frozen state at $-70°$ C. in the Reference Example 3 were slowly thawed under ice cooling, and 30 ng of the DNA containing pTB693 was added to 100 $\mu$l of the suspension thereof. After reaction for 30 minutes under ice cooling, heat shock was given to the reaction product at 42° C. for 90 seconds. The mixture was thereafter cooled with ice for 1 to 2 minutes. SOB medium containing 0.2 ml of 20 mM glucose was added thereto, and cultivation was conducted at 37° C. for 1 hour. The suspension was inoculated on an LB agar plate containing 35 $\mu$g/ml of ampicillin, and cultivated at 37° C. overnight. As a result, colonies of ampicillin-resistant transformants could be obtained from plasmid pTB693.

The above *Escherichia coli* DH1 strain containing plasmid pTB693 was cultivated in 250 ml of LB medium containing 35 $\mu$g/ml of ampicillin [the experimental textbook (1), p.68]. Then, by isolating the plasmid in accordance with the method described in the experimental textbook (1). p.88, about 300 $\mu$g of pTB693 was obtained.

Process 2 (Preparation of Human LT-cDNA)

Fifty (50) $\mu$g of pTB693 plasmid was digested with 100 units of Nsi I and 120 units of Bgl II (Takara Syuzo) at 37° C. for 1 hour, and then subjected to 2% agarose gel electrophoresis. A band of 0.56 Kbp corresponding to the Nsi l-Bgl II fragment containing LT-cDNA was cut out and purified by an RDP minicolumn described in Process 1.

On the other hand, the following 6 oligonucleotide chains coding for the N-terminal peptide (1-20) of LT were chemically synthesized using a Model 380A-DMA synthesizer of Applied Biosystems (U.S.A.) [Tetrahedron Lett., 21, 3243 (1980)]:

The 5'-terminus of LT gene

-continued

```
          1                                              10
          Leu  Pro  Gly  Val  Gly  Leu  Thr  Pro  Ser  Ala—

AATTCT    ATG  CTC  CCT  GGT  GTT  GGC  CTC  ACA  CCT  TCA  GCT—
    GA    TAC  GAG  GGA  CCA  CAA  CCG  GAG  TGT  GGA  AGT  CGA—

(EcoR I)                                                        (Pvu II)

20
Ala  Gln  Thr  Ala  Arg  Gln  His  Pro  Lys  Met

GCC  CAG  ACT  GCC  CGT  CAG  CAC  CCC  AAG  ATG  CA
CGG  GTC  TGA  CGG  GCA  GTC  GTG  GGG  TTC  T (Nsi I)
```

Synthetic oligonucleotides

```
    #1                                       #3
AATTCT    ATG  CTG  CCT  GGT  GTT  GGT |CTG  ACA  CCT  TCA  GCT—
    GA    TAC  GAC  GGA  CCA  CAA  CCA  GAC  TG|T  GGA  AGT  CGA—
    #2                                            #4

#5
GCT  CAG  ACT |GCT  AGA  CAG  CAT  CCT  AAG  ATG  CA
CGA  GTC  TGA  CGA  T|CT  GTC  GTA  GGA  TTC  T
                #6
```

To the mixture of each 1 μg of these chains, 12.5 units of T4 polynucleotide kinase and 1 mM ATP were added, and phosphorylation was conducted at 37° C. for 1 hour. After inactivation at 70° C. for 5 minutes, the mixture was further reacted with 350 units of T4 DNA ligase at 14° overnight. After inactivation at 65° C. for 5 minutes, 45 units of EcoR I (Takara Syuzo) and 35 units of Nsi I were added to the mixture where the reaction was completed (containing about 3.5 μg of DNA), and digestion was carried out at 37° C. for 2 hours. Then, the mixture was subjected to 10% polyacrylamide gel electrophoresis.

A band corresponding to about 70 bp was cut out and purified by an RDP minicolumn.

To 30 ng of the above-mentioned EcoR I-Nsi I fragment of about 70 bp, 110 ng of the Nsi I-Bgl II fragment of 0.56 Kbp was added, and the mixture was reacted in the presence of 35 units of T4 DNA ligase at 14° C. for 2 hours. As to the mixture where the reaction was completed, digestion and trimming were carried out with 6 units of Bgl II and 9 units of EcoR I at 37° C. for 1 hour, whereby cDNA of 0.63 Kbp coding for the whole amino acid sequence of human LT (1-171) could be prepared.

Process 3 (Preparation of pTB692 Plasmid DNA)

Two (2) μg of plasmid ptrp781 was digested with 32 units of Pst I (Takara Syuzo) at 37° C. for 1 hour. After completion of the reaction, TNE buffer [the experimental textbook (1), p.448] and SDS for giving a final concentration of 0.2% were added thereto. Then, extraction with phenol-chloroform and purification were performed.

To 1 μg of Pst I-digested ptrp781 described above, 0.1 mM XTP and 4 units of T4 DNA polymerase were added. After the mixture was reacted at 37° C. for 5 minutes, TNE buffer and SDS were added thereto. Then, extraction with phenolchloroform and purification were carried out.

Next, 0.2 μg of the phosphorylated Bgl II linker described in Process 1 and 35 units of T4 DNA ligase were added to 0.8 μg of the ptrp781 DNA described above, and the mixture was reacted at 14° C. overnight. After inactivation at 65° C. for 5 minutes, the reaction product was trimmed with 30 units of Bgl II, extracted with phenol-chloroform, and further purified by a Sepharose 4B column. Thereafter, 10 units of T4 DNA ligase was added to obtain DNA containing pTB692, followed by transformation of Escherichia coli DH1 strain with the DNA according to the known method described in Process 1. However, an LB agar plate containing 10 μg/ml of tetracycline was used instead of 35 μg/ml of ampicillin. Then, colonies of tetracycline-resistant transformants were obtained. The colonies were cultivated in LB medium comprising 10 μg/ml of tetracycline. pTB692 plasmid was obtained according to the method of Process 1.

Process 4 (Preparation of pTB694 Plasmid DNA)

Fifty-four (54) units of EcoR I and 30 units of Bgl II were added to 10 μg of the pTB692 plasmid DNA described in Process 3, and the mixture was reacted at 5° C. overnight. The reaction product was thereafter purified by 1% agarose gel electrophoresis, and a DNA band of 3.3 Kbp was cut out. To 36 ng of this DNA of 3.3 KBP, 15 ng of the DNA fragment of 0.63 Kbp described in Process 2 was added to obtain DNA containing pTB694 by 10 units of T4 DNA ligase, followed by preparing tetracycline-resistant transformants in accordance with the method described in Process 3. Thus, plasmid pTB694 for expression of human LT (1-171) could be obtained.

EXAMPLE 4

Construction of Human LT
[Lys-Leu-Ala-Leu-Thr-(20-171)]Expression Vector pTB773

Figure 2:
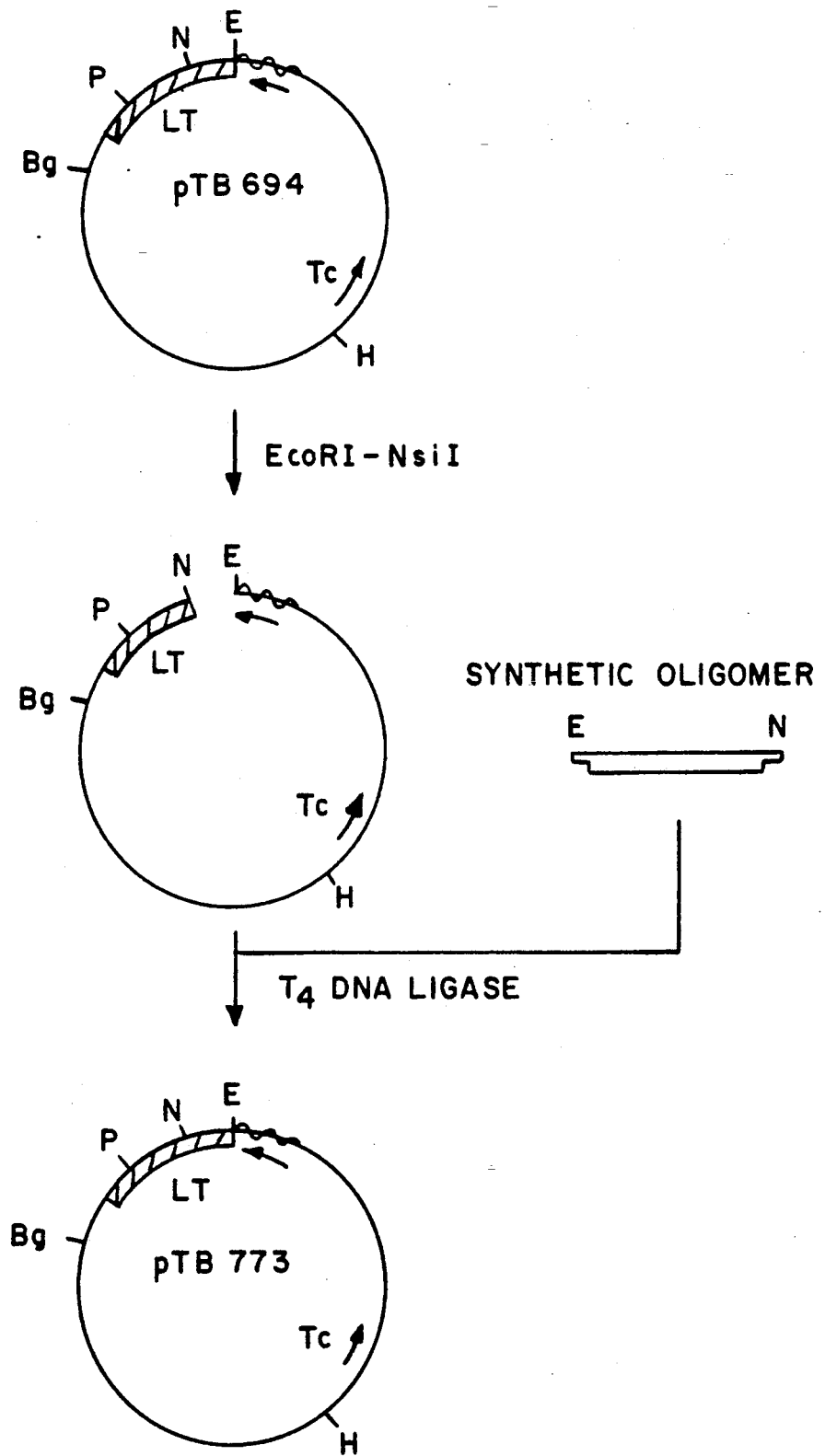

As shown in FIG. 2, the plasmid pTB694 described in Example 3 was digested with restriction enzymes EcoR I and Nsi I to remove the DNA fragment coding for the N-terminal portion of LT. Then, Lys-Leu-Ala-Leu-Thr was coded for in the large fragment thus obtained, and an oligonucleotide containing an EcoR I linker accompanied with ATG was combined therewith by T4 DNA ligase. After inactivation at 65° C. for 5 minutes, reaction product was trimmed with EcoR I and subjected to 0.8% agarose gel electrophoresis.

A main band corresponding to 3.8 Kbp was cut out, and purified by an RDP minicolumn. Then, T4 DNA ligase was added thereto to obtain DNA containing pTB773, with which *Escherichia coli* DH1 strain was transformed according to the known method described in Process 3 of Example 3. Thus, pTB773 plasmid could be obtained from the transformant.

EXAMPLE 5

Construction of Human LT [Ser-Leu-Ala-Leu-(19-171)]Expression Vector pTB775

Similarly to Example 4, after cleaving pTB694 with restriction enzyme EcoR I and Nsi I, Ser-Leu-Ala-Leu was coded for in the large fragment thus obtained, and an oligonucleotide containing an EcoR I linker accompanied with ATG was combined therewith by T4 DNA ligase. In the subsequent procedures, the same methods as those in Example 4 were employed. Thus, pTB775 plasmid could be obtained.

EXAMPLE 6

Construction of Human LT [Lys-Ser-Ala-Leu-Ala-Leu-Ser-Asp-Lys-Pro-(10-171-)]Expression Vector pTB858

Figure 3:
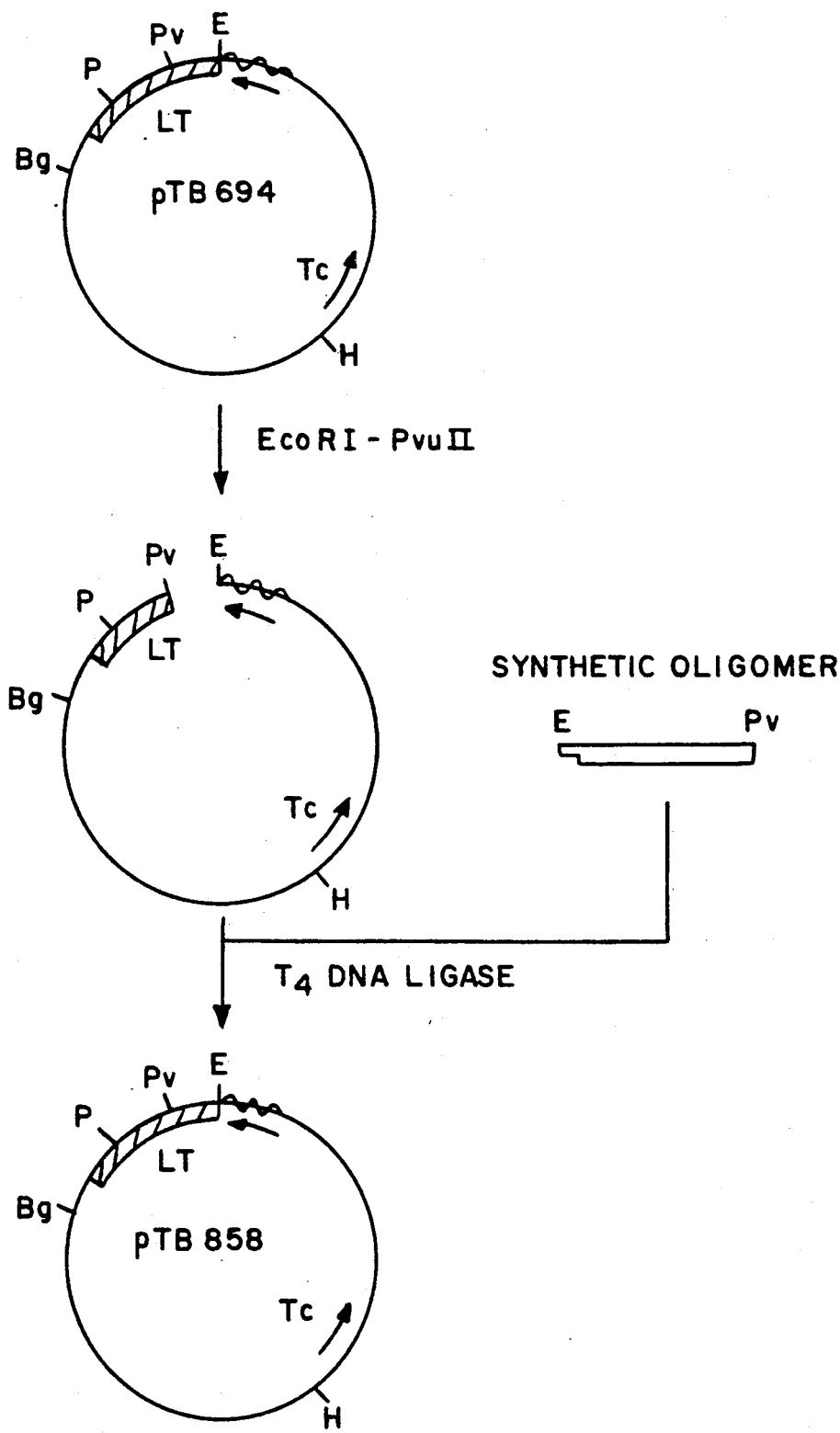

As shown in FIG. 3, after cleaving pTB694 with restriction enzyme EcoR I and Nsi I, Lys-Ser-Ala-Leu-Ala-Leu-Ser-Asp-Lys-Pro was coded for in the large fragment, and an oligonucleotide containing an EcoR I linker accompanied with ATG was combined therewith by T4 DNA ligase. In the subsequent procedures, the same methods as those in Example 4 were employed. Thus, pTB858 plasmid could be obtained.

EXAMPLE 7

Construction of Human LT [Lys-Ser-Ala-Leu-Ala-Leu-Ser-Asp-Lys-Pro-(10-171-)]Expression Vector pTB864

Figure 4:
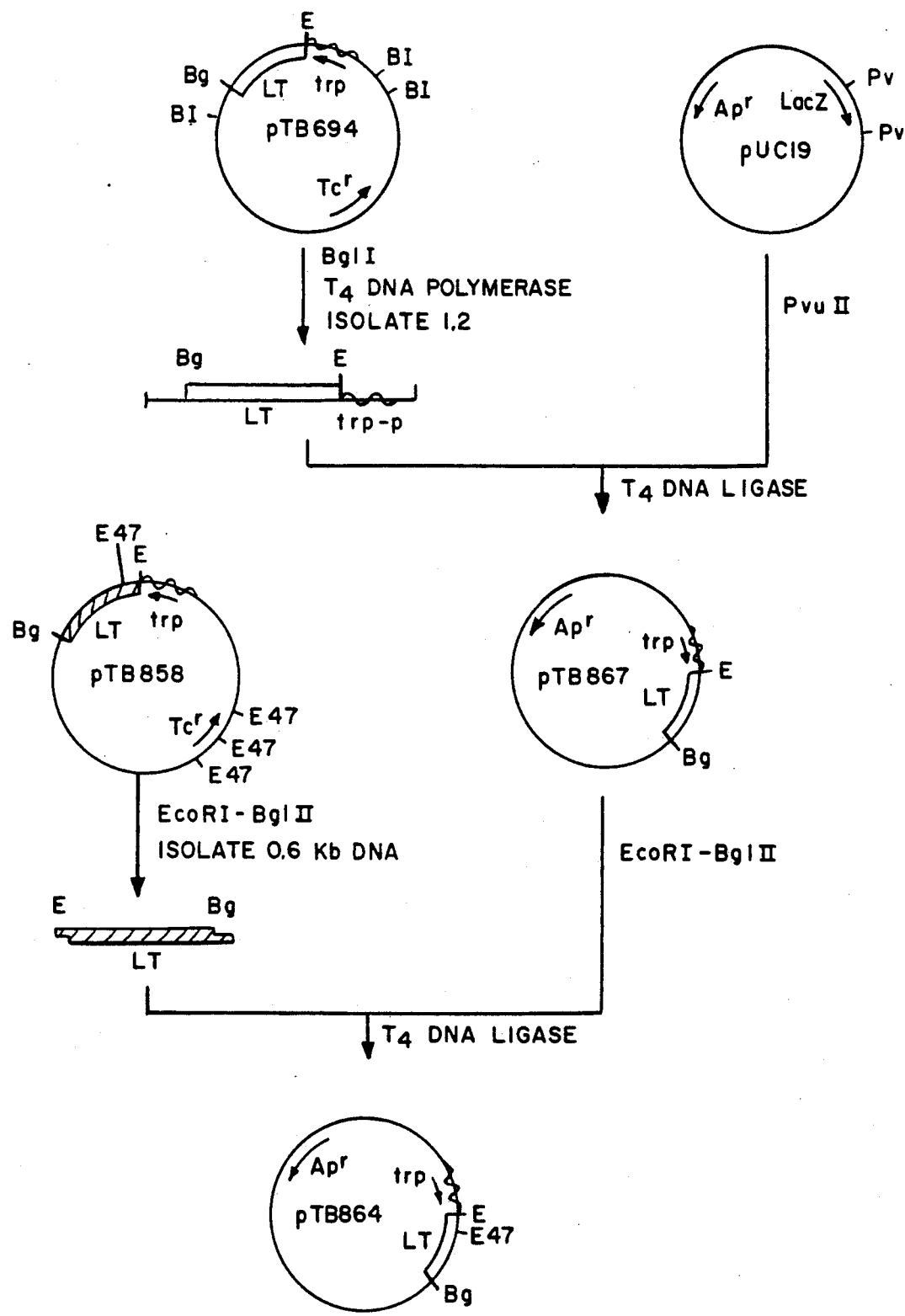

As shown in FIG. 4, after digesting pTB694 with restriction enzyme Bgl I, T4 DNA polymerase was reacted therewith to prepare a DNA fragment of 1.2 Kbp coding for the trp-promoter and the whole amino acid sequence of human LT (1-171). Then, plasmid pUC 19 (Takara Syuzo) was cleaved with Pvu II, followed by addition of the above DNA fragment of 1.2 Kbp and T4 DNA ligase to obtain pTB867.

On the other hand, pTB858 prepared in Example 6 was digested with EcoR I and Bgl II to isolate a DNA fragment of 0.6 Kbp. Similarly, pTB867 was digested with EcoR I and Bgl II, and the above DNA fragment of 0.6 Kbp and T4 DNA ligase were added to the large fragment thus obtained, whereby pTB864 plasmid could be obtained.

EXAMPLE 8

Construction of Human LT [Cys-Ser-Ala-Leu-Ala-(22-171)]Expression Vector pTB860

Similarly to Example 4, after cleaving pTB694 with restriction enzyme Nsi I, T4 DNA polymerase was reacted therewith. After cleaving the reaction product with EcoR I, Cys-Ser-Ala-Leu-Ala was coded for in the large fragment thus obtained, and an oligonucleotide containing an EcoR I linker accompanied with ATG was combined therewith by T4 DNA ligase. In the subsequent procedures, the same methods as those in Example 4 were employed. Thus, pTB860 plasmid could be obtained.

EXAMPLE 9

Construction of Human LT [Cys-Ser-Ala-Leu-Ala-Leu-Ser-Asp-Lys-Pro-(10-171)]Expression Vector pTB865

After digesting pTB864 obtained in Example 7 with EcoR I and Eco 47 III, Cys-Ser-Ala-Leu-Ala was coded for in the large fragment thus obtained, and an oligonucleotide containing an EcoR I linker accompanied with ATG was combined therewith by T4 DNA ligase. In the subsequent procedures, the same methods as those in Example 4 were employed. Thus, pTB865 plasmid could be obtained.

EXAMPLE 10

Construction of Human LT [Lys-Ser-Ala-Leu-Ala-(22-171)]Expression Vector pTB866

After digesting pTB864 with Nsi I, T4 DNA polymerase was reacted therewith. The reaction product was digested with Eco 47 III, and the small fragment was removed therefrom, followed by ring closure with T4 DNA ligase. In the subsequent procedures, the same methods as those in Example 4 were employed. Thus, pTB866 plasmid could be obtained.

EXAMPLE 11

Expression of Human LT in *Escherichia coli* Strain

*Escherichia coli* strain described in Reference Example 3 was transformed by using plasmids pTB694, pTB773, pTB775, pTB858, pTB864, pTB860, pTB865 and pTB866 prepared in Examples 1 and 4 to 10.

The obtained transformant was cultivated in 4 ml of M9-CA medium [the experimental textbook (1), p.69]at 37° C. for 4 hours. After 25 μg/ml of indoleacrylic acid was added thereto, cultivation was further continued for 4 hours. The collected cells were suspended in 0.3 ml of Tris-hydrochloric acid buffer (pH 7.5) containing 0.01% lysozyme and 10% sucrose. The suspension was reacted at 5° C. for 1 hour, and then treated with ultrasonication for 45 seconds, under ice cooling.

The cell extract thus obtained was subjected to the test of the cytotoxic activity against the L929 cell described in Reference Example 1 to measure the activity of LT. The results shown in Table 1 were obtained.

TABLE 1

| | Cytotoxic activity of DH1 transformants against L929 cell | | | | |
|---|---|---|---|---|---|
| Plasmid | Expressed peptide | Colony No. | Cytotoxic activity | | |
| | | | Unit/ml | Average | Ratio |
| pTB694 | LT(1-171) | 1 | $1.1 \times 10^2$ | $1.2 \times 10^2$ | 1 |
| | | 2 | $1.2 \times 10^2$ | | |
| | | 3 | $1.3 \times 10^2$ | | |
| pTB773 | LT[Lys—Leu—Ala—Leu—Thr—(20-171)] | 1 | $2.3 \times 10^2$ | $2.4 \times 10^2$ | 2 |
| | | 2 | $2.4 \times 10^2$ | | |
| | | 3 | $2.5 \times 10^2$ | | |
| pTB775 | L1[Ser—Leu—Ala—Leu—(19-171)] | 1 | $8.4 \times 10^3$ | $8.4 \times 10^3$ | 70 |
| | | 2 | $7.8 \times 10^3$ | | |
| | | 3 | $8.9 \times 10^3$ | | |
| pTB858 | LT[Lys—Ser—Ala—Leu—Ala—Leu—Ser—Asp—Lys—Pro—(10-171)] | 1 | $1.4 \times 10^2$ | $2.0 \times 10^2$ | 1.7 |
| | | 2 | $7.8 \times 10$ | | |
| | | 3 | $4.0 \times 10^2$ | | |
| pTB864 | LT[Lys—Ser—Ala—Leu—Ala—Leu—Ser—Asp— | 1 | $9.0 \times 10^3$ | $8.8 \times 10^3$ | 73 |
| | | 2 | " | | |
| | | 3 | $8.4 \times 10^3$ | | |

TABLE 1-continued

Cytotoxic activity of DH1 transformants against L929 cell

| Plasmid | Expressed peptide | Colony No. | Cytotoxic activity Unit/ml | Average | Ratio |
|---|---|---|---|---|---|
| | Lys—Pro—(10-171)] | | | | |
| pTB860 | LT[Cys—Ser—Ala—Leu—Ala—(22-171)] | 1 | $1.9 \times 10^4$ | $1.4 \times 10^4$ | 117 |
| | | 2 | $.1.2 \times 10^4$ | | |
| | | 3 | $1.1 \times 10^4$ | | |
| pTB865 | LT[Cys—Ser—Ala—Leu—Ala—Leu—Ser—Asp—Lys—Pro—(10-171)] | 1 | $6.0 \times 10^4$ | $5.9 \times 10^4$ | 492 |
| | | 2 | $5.9 \times 10^4$ | | |
| | | 3 | " | | |
| pTB866 | LT[Lys—Ser—Ala—Leu—Ala—(22-171)] | 1 | $2.2 \times 10^5$ | $2.2 \times 10^5$ | 1833 |
| | | 2 | $2.4 \times 10^5$ | | |
| | | 3 | $2.0 \times 10^5$ | | |

EXAMPLE 12

Purification of Human LT

*Escherichia coli* strain DH1 for transformation described in Reference Example 3 was transformed by using plasmid pTB865 prepared according to the method described in Example 9. After cultivation of the obtained transformant by the method described in Example 11, the cells were disrupted by treatment of lysozyme and ultrasonication, whereby an extract containing human LT was obtained.

Then, the extract was added to a DEAE-Sepharose CL-6B column (Pharmacia) equilibrated with 5 mM phosphate buffer (pH 8.0), and washed with the same buffer, followed by elution with the same buffer containing 0.1 m NaCl to provide a roughly purified solution.

After being adjusted to pH 6.0 by hydrochloric acid, the roughly purified solution described above was added to a Blue Sepharose CL-6B column equilibrated with 20 mM phosphate buffer (pH 6.0) containing 0.1 M NaCl, and washed enough, followed by elution with 20 mM phosphate buffer (pH 8.0) containing 0.5 M NaCl.

The eluate was further subjected to gel filtration by a Sephacryl S-200 column equilibrated with 20 mM phosphate-NaCl buffer (pH 7.3). Thus, a human LT sample having a specific activity of $5.7 \times 10^6$ U/mg was obtained.

EXAMPLE 13

Construction of Human LT [Phe-(25-171)]Expression Vector pTB953

(1) Preparation of Rabbit Anti-Human LT-C-Terminal Peptide Antibody

A 10 mg/5 ml aqueous solution of the human LT-C-terminal peptide (152-171) prepared by using a peptide synthesizer (Model 430A manufactured by Applied Biosystems) according to a known solid phase synthesis method was added to a 40 mg/5 ml aqueous solution of bovine thyroglobulin (BTG). After slight ultrasonication, 1 ml of a 2% glutalaldehyde (GLA) solution was gently added dropwise thereto under ice cooling and reacted for 5 hours. The mixture was dialyzed 3 times against every 3 l of a physiological saline, and stored under a frozen condition for use as an immunogen.

To 4 mg of the peptide-BTG conjugate in 1.5 ml of a physiological saline, the same volume of Freund's complete adjuvant was added. The mixture was subcutaneously administered to rabbits (♂ n=3: 1.3 mg/1 ml/rabbit) at their backs and hind-limb palms to initiate immunization. Supplemental immunization was carried out by inoculating the immunogen to which the same volume of Freund's incomplete adjuvant was added, 5 times at 4-week intervals.

After 7 to 10 days from the final immunization, the blood is collected from the aural veins to obtain the anti-serum by centrifugation.

Specific antibodies were prepared by applying the above-mentioned serum to salting out and column chromatography and further purifying the obtained antibody IgG fraction by affinity chromatography using an insolubilized human LT-cellulofine column, according to a known method. That is to say, the rabbit anti-human LT-IgG fraction was added to a human LT-linked column equilibrated with 0.02 M borate buffer (pH 8.0) containing 0.15 M NaCl, and thoroughly washed, followed by elution with 0.02 M glycine-hydrochloric acid buffer (pH 2.3). Thus, specific neutralizing antibodies LT-R1, LT-R2 and LT-R3 having high affinity for human LT were obtained.

(2) Construction of pTB953

Figure 5:
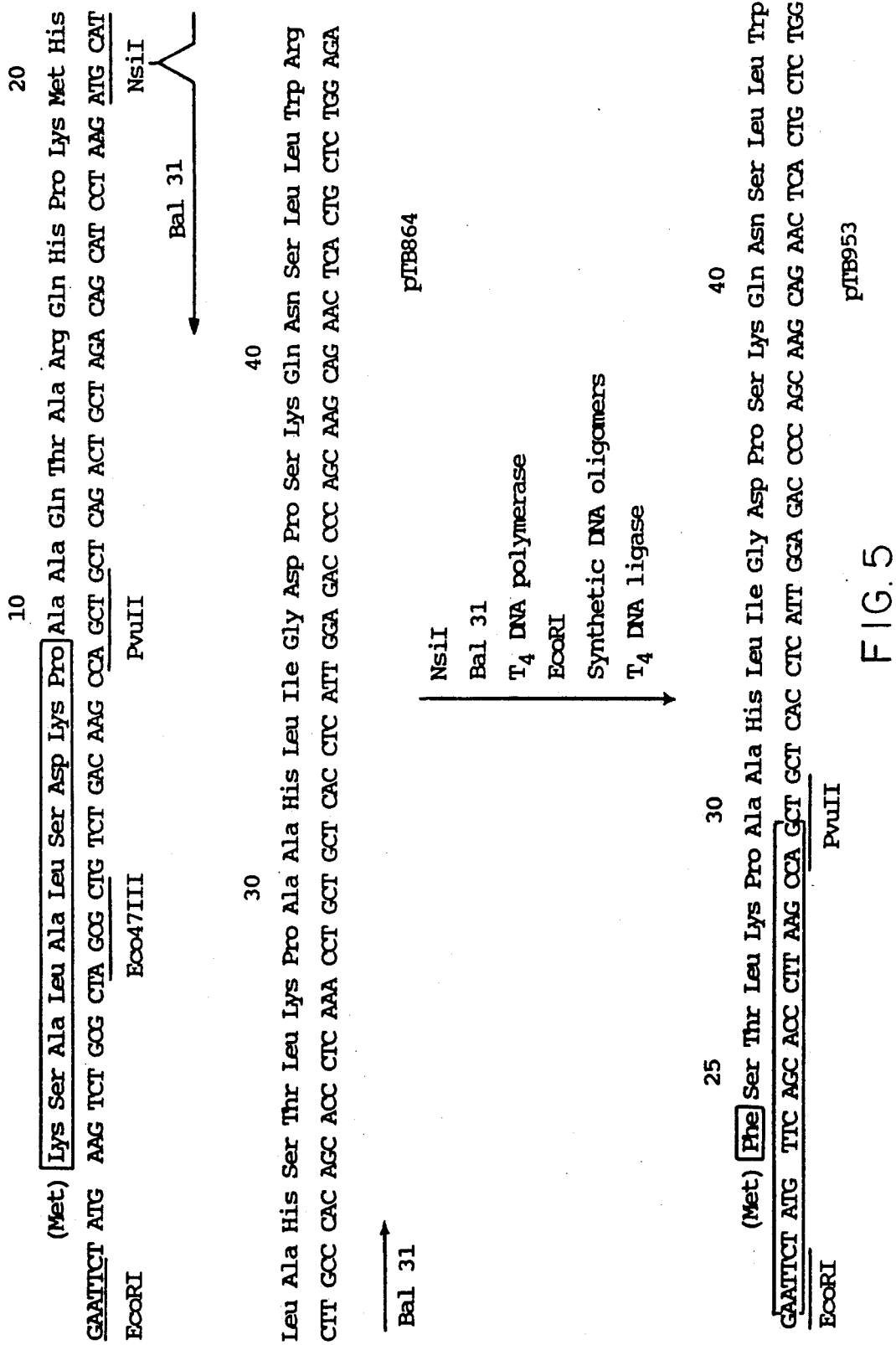

As shown in FIG. 5, after cleaving pTB864 obtained in Example 7 with Nsi I, Bal 31 (Takara Syuzo) was added thereto to remove the terminal oligonucleotide by digestion. Then, T4 DNA polymerase was reacted therewith to change the termini of the product to flush ends, followed by cleavage with EcoR I. Phe-Ser-Thr-Leu-Lys-Pro was coded for in the DNA large fragment thus obtained, and an oligonucleotide containing an EcoR I linker accompanied with ATG was combined therewith by T4 DNA ligase.

After *Escherichia coli* DH1 strain was transformed using the plasmid thus obtained, a cell extract was prepared according to the method described in Example 11. Then, a LT expression strain was selected by immunoblotting using rabbit anti-human LT-C-terminal peptide antibody LT-R2, and further the plasmid DNA was prepared from the positive expression strain, followed by confirmation of the nucleotide sequence, whereby plasmid pTB953 expressing the desired human LT [Phe-(25 - 171)]could be obtained.

EXAMPLE 14

Construction of Human LT [Lys-Ser-Ala-Leu-Ala-Leu-Ser-Asp-(28-171)]Expression Vector pTB1004

After digesting pTB953 obtained in Example 13 with EcoR I and Pvu II, Lys-Ser-Ala-Leu-Ala-Leu-Ser-Asp-Lys-Pro was coded for in the DNA large fragment thus obtained, and an oligonucleotide containing an EcoR I linker accompanied with ATG was combined therewith by T4 DNA ligase. In the subsequent procedures, the same methods as those in Example 4 were employed to prepare a plasmid, and there was confirmed the presence of Nhe I and Eco 47 III cleavage sites derived from the synthetic oligonucleotide as shown in FIG. 6, whereby a desired pTB865 plasmid could be obtained.

EXAMPLE 15

Construction of Human LT [Cys-Ser-Ala-Leu-Ala-Leu-Ser-Asp-(28-171)]Expression Vector pTB1005

After digesting pTB1004 obtained in Example 14 with EcoR I and Eco 47 III, Cys-Ser-Ala-Leu was coded for in the DNA large fragment thus obtained, and an oligonucleotide containing an EcoR I linker accompanied with ATG was combined therewith by T4 DNA ligase. In the subsequent procedures, the same methods as those in Example 4 were employed to prepare a plasmid. There could be obtained a desired pTB1005 plasmid which did not contain any Nhe I cleavage site (see FIG. 6) and contained an Eco 47 III cleavage site as shown in FIG. 7.

EXAMPLE 16

Construction of Human LT [Cys-Ser-Gly-Phe-Leu-Gly-Ser-(27 –171)]Expression Vector pTB1006

After digesting pTB953 obtained in Example 13 with EcoR I and Pvu II, Cys-Ser-Gly-Phe-Leu-Gly-Ser-Leu-Lys-Pro was coded for in the DNA large fragment thus obtained, and an oligonucleotide containing an EcoR I linker accompanied with ATG was combined therewith by T4 DNA ligase. In the subsequent procedures, the same methods as those in Example 4 were employed to prepare a plasmid. Thus, there could be obtained a desired pTB1006 plasmid having an Acc III cleavage site as shown in FIG. 8.

EXAMPLE 17

Construction of Human LT [Cys-Ser-Gly-Phe-Leu-Gly-Ser-Leu-Lys-Pro-(10–171-)[Expression Vector pTB1007

After digesting pTB867 obtained in Example 7 with EcoR I and Pvu II, Cys-Ser-Gly-Phe-Leu-Gly-Ser-Leu-Lys-Pro was coded for in the DNA large fragment thus obtained, and an oligonucleotide containing an EcoR I linker accompanied with ATG was combined therewith by T4 DNA ligase. In the subsequent procedures, the same methods as those in Example 4 were employed to prepare a plasmid. Thus, there could be obtained a desired pTB1007 plasmid having an Acc III cleavage site as shown in FIG. 9.

EXAMPLE 18

Expression of Human LT in *Escherichia coli* Strain (2)

There were obtained according to the method described in Example 11 extracts of *Escherichia coli* transformants prepared in Examples 14 to 17, using plasmids pTB1004, pTB1005, pTB1006 and pTB1007, respectively. Then, the extracts were subjected to the test of the cytotoxic activity against the L929 cell described in Reference Example 1. The results shown in Table 2 were obtained.

EXAMPLE 19

Purification of Novel Human LT mutein (2)

(1) Construction of Human LT (21-171) Expression Vector pTB622

The plasmid pTB618 prepared above was cleaved by restriction enzymes NsiI (Takara Syuzo) and BamHI, and a DNA fragment of 1.1 kilo base pair (hereinafter referred to as Kbp) containing the LT gene was separated. T4 DNA polymerase (PL Inc.) was reacted with the DNA fragment to change the termini of the product to flush ends. Thereafter, an EcoRI linker accompanied with ATG of 16 mer (AACATGAATTCATGTT) was ligated therewith by T4 DNA ligase for adjusting the frame. After T4 DNA ligase was inactivated by heat treatment at 65° C. for 10 minutes, digestion was carried out with restriction enzyme EcoRI, and a DNA fragment of 0.6 Kbp containing the LT gene linked with the linker was separated by agarose electrophoresis.

The plasmid ptrp781 described in T. Kurokawa et al., *Nucl. Acids Res.* 11, 3077 (1983) was cleaved by restriction enzyme EcoRI, and the phosphate of the 5'-terminus was removed by alkaline phosphatase treatment. The thus obtained DNA fragment was mixed with the LT DNA fragment of 0.6 Kbp linked with the EcoRI linker accompanied with ATG, and T4 DNA ligase was allowed to act on e mixture, whereby human LT expression vector pTB622 for *Escherichia coli* was constructed in which the LT gene was inserted downstream of the tryptophan promotor.

*Escherichia coli* DH1 strain was transformed by using plasmid pTB622 prepared as described above.

The transformant thus obtained was cultivated in 2.5 l of M9-CA medium [the experimental textbook (1), p. 69] at 37° C. for 4 hours. After 25 μg/ml of indolylacrylic acid was added thereto, cultivation was further continued for 4 hours. The cells were collected and suspended in 100 ml of Tris-hydrochloric acid buffer (pH 7.5) containing 0.01% lysozyme and 10% sucrose. The suspension was reacted at 5° C. for 1 hour, and then treated with ultrasonication for 5 minutes under ice cooling. After centrifugation, the extract was added to a DEAE-Sepharose CL-6B column (Pharmacia) equilibrated with 5 mM phosphate buffer (pH 8.0), and washed with the same buffer, followed by elution with the same buffer containing 0.1 M NaCl to provide a roughly purified solution having a specific activity of $7.8 \times 10^5$ U/mg.

After adjusting to pH 6.0 by hydrochloric acid, the roughly purified solution described above was added to a Blue Sepharose CL-6B column equilibrated with 5 mM phosphate buffer (pH 6.0) containing 0.1 M NaCl, and thoroughly washed, followed by elution with 5 mM phosphate buffer (pH 8.0) containing 0.5 M NaCl. The specific activity of the eluate was $7.4 \times 10^5$ U/mg.

The eluate was further subjected to gel filtration by a Sephacryl S-200 column equilibrated with 5 mM phosphate buffer (pH 7.3) to obtain a purified solution having a specific activity of $1.6 \times 10^7$ U/mg.

(2) Preparation of Mouse Anti-Human LT Monoclonal Antibody

To 200 μg of the purified human LT sample described above in 1 ml of a physiological saline, the same volume of Freund's complete adjuvant was added and fully emulsified. The emulsion was then administered to BALB/c mice (♀, n=10 : 20 μg/0.2 ml/mouse) intraperitoneally and subcutaneously at their backs, and supplemental immunization was carried out at an interval of 3 weeks. After the supplemental immunization was conducted 4 times, the same LT antigen solution (50 μg/0.1 ml of physiological saline/mouse) was intravenously administered to the individual which showed the highest serum antibody titer after 2 weeks.

The spleen was taken out of the mouse after 3 days from the final immunization, and a spleen cell suspension containing about $10^8$ cells was prepared by a conventional method. Then, $2 \times 10^7$ mouse myeloma cells (P3UI) were added thereto, and cell fusion was conducted by using PEG 6000 according to the method of Köler and Milstein [*Nature*, 256, 495 (1975)].

After completion of the fusion, the cell mixture was suspended in so-called HAT medium containing hypoxanthine, aminopterin and thymidine, and cultivated for 10 days. Then, immediately after selection of parent cells was completed, HAT medium was substituted for HT medium from which aminopterin was eliminated, and the cultivation was continued.

The antibody titer of hybridoma culture supernatants was determined by ELISA using a microplate in which purified human LT was adsorbed on a solid phase. After 10 to 20 days from the fusion, hybridomas and an antibody which could bind to human LT were observed. The hybridomas having particularly high binding activity were cloned by the limiting dilution method.

Similarly, the cloned hybridoma culture supernatants were screened by ELISA, and the supernatants having high binding activity to human LT were selected. For these supernatants, the neutralization ability against the human LT activity was measured by using the test of the cytotoxic activity against L929 cells described in Reference Example 1. Namely, to 100 units/ml of human LT, the same amount of the hybridoma culture supernatant was added and reacted for 1 hour, followed by the test of the cytotoxic activity against L929.

As a result, there were obtained MoAB-producing hybridomas LT3-11 and LT3-135 which were capable of linking with human LT and neutralizing the cytotoxic activity against them. Their immunoglobulin class and subclass were examined by the Ouchterlony test. They were found to belong to $IgG_{2b}$ and $IgG_{2a}$, respectively.

The cloned hybridoma cells were cultivated in Iskove-Ham mixture medium (I-H medium) containing 10% FCS at 37° C. by using a 5% $CO_2$ incubator to obtain an antibody from the supernatant thereof.

On the other hand, in order to obtain a large amount of antibody, $5\times10^6$ hybridoma cells were intraperitoneally inoculated into a mouse to which 0.5 ml of mineral oil had been intraperitoneally administered in advance. After about 10 to 15 days, retention of ascites was observed.

The antibody was purified by fractionation with 45–50% saturated ammonium sulfate and DEAE-cellulose and protein A column chromatography, according to a conventional method.

(3) Preparation of Cell Extract

*Escherichia coli* transformant was prepared according to the method described in Example 11 by using pTB860 obtained in Example 8, and further an extract containing human LT was obtained. This crude extract was salted out with 40% saturated ammonium sulfate, and then dialyzed against 20 mM phosphate buffer (pH 8.0) containing 1 mM dithiothreitol.

(4) Purification by Antibody Column Chromatography

An immuno-affinity column obtained by combining mouse anti-human LT monoclonal antibody LT3-11 with Formylcellulofine (sold by Seikagaku Kougyou) was equilibrated with 20 mM phosphate buffer (pH 8.0) containing 0.15 M NaCl and 5 mM EDTA. Then, the cell extract obtained in (3) was added to the above column and washed with the same buffer. Human LT adsorbed in the column was eluted with 20 mM carbonate buffer (pH 12.5) containing 0.15 M NaCl and immediately neutralized with 0.1 N HCl, followed by dialysis against 20 mM phosphate buffer (pH 8.0) containing 0.15 M NaCl and 5 mM EDTA.

(5) Purification by Gel Filtration Column Chromatography

The human LT-containing solution eluted from the above-mentioned antibody column was condensed by ultrafiltration, and then purified and separated by a Sephacryl S-200 column equilibrated with 20 mM phosphate buffer (pH 8.0) containing 0.15 M NaCl and 5 mM EDTA.

All operations (3) to (5) were performed at low temperatures (5° to 10° C.) From 42 g by wet weight of the cells, 3.3 mg of a purified human LT sample was obtained.

EXAMPLE 20

Preparation of Human LT-Human Transferrin (hTf) Conjugate (1) Preparation of Maleimidated hTf Eight-fold moles of GMBS dissolved in dimethylformamide (DMF) was added to 5 mg of commercial hTf, and reacted with each other at 30° C. for 1 hour. Then, the reaction mixture was subjected to a Sephadex G-25 equilibrated with 0.1 M phosphate buffer (pH 6.5) to remove the unreacted maleimidation reagent. In the maleimidated hTf were introduced.

(2) Preparation of Human-hTf Conjugate

One (1) mg of human LT [Cys-Ser-Ala-Leu-Ala-(22-711)]obtained in Example 19 was dissolved in 1 ml of 0.1 M phosphate buffer (pH 6.5) containing 5 mM EDTA, and then 1 mg of the maleimidated hTf obtained in item (1) was added thereto. After reaction at 4° C. overnight, purification and separation were conducted on a Sephacryl S-200 column equilibrated with 10 mM phosphate buffer to obtain 1.5 mg of a human LT-hTf conjugate.

(3) Cytotoxic activity of Human LT-hTf Conjugate

Using a 96-well microplate, $1.0\times10^4$ tumor cells were added to 50μl of each of human LT-hTf conjugate-containing solutions of various concentrations and cultivated at 37° C. for 3 days. After completion of the cultivation, the number of live cells was determined by the method described in Reference Example 1 to evaluate the cytotoxic activity of the conjugate.

The results are as shown in Table 3. The human LT-hTf conjugate exhibited a cytotoxity against a human LT-resistant and human transferrin receptor-positive tumor cell.

EXAMPLE 21

Preparation of Human LT-Anti-hTfR Antibody Conjugate (1) Purification of hTfR Human placental tissue (1.5 kg) was finely cut, blended in phosphate-buffered saline (PBS) (pH 7.5) and centrifuged. The residue was homogenized in PBS containing 4% Triton X-100, treated with sonication and then centrifuged. The supernatant was subjected to salting out using ammonium sulfate in an amount of about 32 g per 100 ml of the supernatant, and then allowed to pass through an anti-human transferrin (hTf) antibody-bound column. The column was washed with phosphate buffer (PB) (pH 7.5) containing 0.5 M NaCl and then human transferrin receptor (hTfR) was eluted by 0.02 M glycine buffer (pH 10.0) containing 0.5 M NaCl and 0.5% Triton X-100. The hTfR fractions were further allowed to pass through an hTf-bound column. The column was washed with PB containing 1 M NaCl, and then hTfR was eluted by 0.05 M glycine buffer (pH 10.0) containing 1 M NaCl and 1% Triton X-100 to obtain a purified hTfR sample (about 1.5 mg).

(2) Immunization and Cell Fusion

Immunization and cell fusion were conducted in accordance with the methods described in Example 19-(2).

(3) Selection and Cloning of Hybridoma

Commercially available rabbit anti-mouse IgG antibody (20 μg/ml, 100 μl) was poured into each of 96 wells of a microplate, and allowed to stand at 4° C. overnight. PBS (pH 7.3) containing 2% BSA was added to the wells to prepare a sensitized plate.

The purified hTfR sample obtained as above (1) was labeled with horseradish peroxidase (HRP) and subjected to the ELISA in accordance with a conventional methods (Kitagawa: Organic Synthetic Chemistry), 42, 283 (1984)]. Thus, the supernatant of hybridoma culture was added to the sensitized plate for the above second antibody and allowed to react at room temperature for 2 hours. After the plate was washed with PBS, hTfR labeled with HRP was added and allowed to react at room temperature for 2 hours.

After the plate was washed, 0.1 M citrate buffer containing ortho-phenylenediamine and $H_2O_2$ and then the enzymatic reaction was conducted at room temperature. After the reaction was terminated with 1 N sulfuric acid, color development at 492 nm was measured by Multiscan (Flow).

The hybridoma having a strong binding activity was cloned by the limiting dilution method to obtain hybridoma 22C6 which could produce anti-hTfR antibody. The antibody of which the subclass was IgG has a high affinity to human tumor cell K562.

(4) Preparation of Maleimidated Antibody

Mouse anti-hTfR monoclonal antibody 22C6 was maleimidated according to the method described in (1) of Example 20. A conjugate in which about 7.7 maleimide groups per molecule of the antibody were introduced was obtained.

(5) Preparation of Human LT-Anti-hTfR Antibody Conjugate

According to the method described in (2) of Example 20, 1 mg of human LT was reacted with 1.5 mg of the maleimidated antibody, and the reaction product was subjected to a Sephacryl S-200 column for purification and isolation, whereby 1.9 mg of a human LT-anti-hTfR antibody conjugate was obtained.

(6) Cytotoxic activity of Human LT-anti-hTfR Antibody Conjugate

The cytotoxic activity of the human LT-anti-hTfR antibody conjugate was determined according to the method described in (3) of Example 20.

The results are as shown in Table 3. The human LT-hTf conjugate exhibited a cytotoxicity against a human LT-resistant and hTfR-positive tumor cell.

TABLE 2

Cytotoxic activity of DH1 transformants against L929 cell

| Plasmid | Expressed peptide | Colony No. | Cytotoxic activity Unit/ml | Average | Ratio |
|---|---|---|---|---|---|
| pTB694 | LT(1-171) | 1 | $1.1 \times 10^2$ | $1.2 \times 10^2$ | 1 |
| | | 2 | $1.2 \times 10^2$ | | |
| | | 3 | $1.3 \times 10^3$ | | |
| pTB1004 | LT[Lys—Ser—Ala—Leu—Ala—Leu—Ser—Asp—(28-171)] | 1 | $1.6 \times 10^5$ | $1.7 \times 10^5$ | 1417 |
| | | 2 | $1.6 \times 10^5$ | | |
| | | 3 | $2.0 \times 10^5$ | | |
| pTB1005 | LT[Cys—Ser—Ala—Leu—Ala— | 1 | $2.1 \times 10^3$ | $2.5 \times 10^3$ | 21 |
| | | 2 | $2.4 \times 10^3$ | | |

TABLE 2-continued

Cytotoxic activity of DH1 transformants against L929 cell

| Plasmid | Expressed peptide | Colony No. | Cytotoxic activity Unit/ml | Average | Ratio |
|---|---|---|---|---|---|
| | Leu—Ser—Asp—(28-171)] | 3 | $3.0 \times 10^3$ | | |
| pTB1006 | LT[Cys—Ser—Gly—Phe—Leu—Gly—Ser—(27-171)] | 1 | $1.1 \times 10^5$ | $1.2 \times 10^5$ | 1000 |
| | | 2 | $1.2 \times 10^5$ | | |
| | | 3 | $1.4 \times 10^5$ | | |
| pTB1007 | LT[Cys—Ser—Gly—Phe—Leu—Gly—Ser—Leu—Lys—Pro—(10-171)] | 1 | $1.0 \times 10^4$ | $1.3 \times 10^4$ | 108 |
| | | 2 | $1.2 \times 10^4$ | | |
| | | 3 | $1.6 \times 10^4$ | | |

TABLE 3

Cytotoxic activity of human LT-hTf conjugate and human LT-anti-hTfR antibody conjugate

| Cytotoxic substance | | % Cytotoxicity[4] | | |
|---|---|---|---|---|
| | | K562 cell | LU99 cell | P388 cell |
| Human LT[1] | 0.8 ng/ml | 5 | 2 | 2 |
| | 3.1 ng/ml | 3 | 12 | 1 |
| | 12.5 ng/ml | 7 | 18 | 6 |
| hTf | 2.0 ng/ml | 0 | −1 | −4 |
| | 8.0 ng/ml | −2 | −3 | −7 |
| Anti-hTfR antibody 22C6[2] | 5.0 ng/ml | 2 | 1 | 5 |
| | 20.0 ng/ml | 0 | 8 | 4 |
| Human LT-hTf conjugate | 0.8 ng/ml[3] | 14 | 15 | 5 |
| | 3.1 ng/ml | 28 | 34 | 18 |
| | 12.5 ng/ml | 35 | 44 | 18 |
| Human LT-anti-hTfR antibody conjugate | 0.8 ng/ml[3] | 12 | 3 | 2 |
| | 3.1 ng/ml | 24 | 22 | 7 |
| | 12.5 ng/ml | 43 | 37 | 16 |

[1] Human LT [Cys—Ser—Ala—Leu—Ala—(22-171)]: described in Example 19.
[2] Described in Example 21.
[3] Converted to amount of human LT.
[4] K562: human leukemia cell (hTfR-positive). LU99: human lung cancer cell (hTfR-positive). P388: mouse leukemia cell (hTfR-negative)

The accession numbers in the deposition institutes of the strains described in the present specification, namely DH1 or C600 strains containing plasmid pTB618, pTB622, ptrp781, pTB773, pTB775, pTB858, pTB860, pTB864, pTB865, pTB866, pTB953, pTB1004, pTB1005, pTB1006 or pTB1007 (*E. coli* DH1 /pTB618, *E. coli* C600/pTB622, *E. coli* DH1 /ptrp781, *E. coli* DH1 /pTB773, *E. coli* DH1 /pTB775, *E. coli* DH1 /pTB858, *E. coli* DH1 /pTB860, *E. coli* DH1 /pTB864, *E. coli* DH1 /pTB865, *E. coli* DH1 /pTB866, *E. coli* DH1 /pTB953, *E. coli* DH1 /pTB1004, *E. coli* DH1 /pTB1005, *E. coli* DH1 /pTB1006, *E. coli* DH1 /pTB1007) and animal cells (mouse-mouse hybridoma LT 3-11 and mouse-mouse hybridoma 22C6) are as shown in Table 4.

TABLE 4

| Microorganism & Animal Cell | IFO (IFO No.) | FRI (FERM No.) |
|---|---|---|
| *Escherichia coli* DH1/pTB618 | 14542 | BP-1587 |
| *Escherichia coli* C600/pTB622 | 14544 | BP-1589 |
| *Escherichia coli* DH1/ptrp781 | 14546 | BP-1591 |
| *Escherichia coli* DH1/pTB773 | 14732 | BP-1832 |
| *Escherichia coli* DH1/pTB775 | 14733 | BP-1833 |
| *Escherichia coli* DH1/pTB858 | 14734 | BP-1834 |
| *Escherichia coli* DH1/pTB860 | 14735 | BP-1835 |
| *Escherichia coli* DH1/pTB864 | 14736 | BP-1836 |
| *Escherichia coli* DH1/pTB865 | 14737 | BP-1837 |
| *Escherichia coli* DH1/pTB866 | 14738 | BP-1838 |

TABLE 4-continued

| Microorganism & Animal Cell | IFO (IFO No.) | FRI (FERM No.) |
|---|---|---|
| Escherichia coli DH1/pTB953 | 14826 | BP-2282 |
| Escherichia coli DH1/pTB1004 | 14827 | BP-2283 |
| Escherichia coli DH1/pTB1005 | 14828 | BP-2284 |
| Escherichia coli DH1/pTB1006 | 14829 | BP-2285 |
| Escherichia coli DH1/pTB1007 | 14830 | BP-2286 |
| Mouse-mouse hybridoma LT3-11 | 50167 | BP-1813 |
| Mouse-mouse hybridoma 22C6 | 50172 | BP-2054 |

IFO: The Institute for Fermentation, Osaka, Japan
FRI: Fermentation Research Institute, Agency of Industrial Science and Technology, Ministry of International Trade and Industry, Japan The above-identified deposits at the FRI were made under the Budapest Treaty in a depository affording permanence of the deposit (at least 30 years) and ready accessibility thereto by the public if a patent is granted, under condition's which assure:
(a) that access to the deposit will be availability to the Commissioner of Patents or his designee under 37 C.F.R. 1.14 and 35 U.S.C. 122 and
(b) that all restrictions (if any) on the availability to the public of the deposit will be irrevocably recovered upon the grant of a patent (at least 30 years).

The following references, which are referred to for their disclosures at various points in this application, are incorporated herein by reference.
Nature, 312, 721 (1984)
Nature, 312, 724 (1984)
Cancer and Chemotherapy, 13, 3491 (1986)
Oncologia, 20, 105 (1987)
Biotech., 5, 335 (1987)
Therapeu. Res., 7, 275 (1987)
J. Exp. Med., 162, 1099 (1985)
Genetic Engineering, 3. 1 (1981)
Molecular Cloning, A Laboratory Manual, Cold Spring Harbor Laboratory, p.312 & 326(1982)
Proc. Natl. Acad. Sci. U.S.A., 69, 2110 (1972)
Experiments in Molecular Genetics, 431 - 433, Cold Spring Harbor Laboratory, New York, 1972)
Pharmacol. Rev., 29, 103 (1978)
Organic Synthetic Chemistry, 42, 283 (1984)
Clin. Immunol. Immunopathol., 46, 100 (1988)
Proc. Natl. Acad. Sci. U.S.A., 79, 626 (1982)
Gene Manipulation Experimental Method, Kodansha (Japan).
J. Immunol., 126, 235 (1981)
J. Immunol. Methods, 70, 257 (1984)
Mol. Cell. Biol., 2, 161 (1982)
Mol. Cell. Biol., 3, 280 (1983)
Proc. Natl. Acad. Sci. U.S.A., 72, 3961 (1975)
Nucleic Acids Res., 7, 1513 (1979)
Nucleic Acids Res., 9, 309 (1981)
Tetrahedron Lett., 21, 3243 (1980)
Nucleic Acids Res., 11, 3077 (1983)
Nature, 256, 495 (1975)].

We claim:
1. A Lymphotoxin protein comprising the following amino acid sequence:

H-(Met)n-$R_1$-$R_2$-$(R_3)_m$-Lys-Pro-Ala -Ala-His-Leu-Ile-Gly-Asp-Pro-Ser-Lys -Gln-Asn-Ser-Leu-Leu-Trp-Arg-Ala-Asn -Thr-Asp-Arg-Ala-Phe-Leu-Gln-Asp-Gly -Phe-Ser-Leu-Ser-Asn-Asn-Ser-Leu-Leu -Val-Pro-Thr-Ser-Gly-Ile-Tyr-Phe-Val -Tyr-Ser-Gln-Val-Val-Phe-Ser-Gly-Lys -Ala-Tyr-Ser-Pro-Lys-Ala-Thr-Ser-Ser -Pro-Leu-Tyr-Leu-Ala-His-Glu-Val-Gln -Leu-Phe-Ser-Ser-Gln-Tyr-Pro-Phe-His -Val-Pro-Leu-Leu-Ser-Ser-Gln-Lys-Met -Val-Tyr-Pro-Gly-Leu-Gln-Glu-Pro-Trp -Leu-His-Ser-Met-Tyr-His-Gly-Ala-Ala -Phe-Gln-Leu-Thr-gln-Gly-Asp-Gln-Leu -Ser-Thr-His-Thr-Asp-Gly-Ile-Pro-His -Leu-Val-Leu-Ser-Pro-Ser-Thr-Val-Phe -Phe-Gly-Ala-Phe-Ala-Leu-OH wherein R, is Cys, Lys, Ser, Cys-Ser or Lys-Ser; $R_2$ is Ala-Leu-Ala, Leu-Ala-Leu, Leu-Ala-Leu-Thr, Ala-Leu-ala-Leu, Ala-Leu-Ala-Leu-Ser-Asp-Lys-Pro, Ala-Leu-Ala-Leu-Ser-Asp, Gly-Phe-Leu-Gly-Ser, Gly-Phe-Leu-Gly-Ser-Leu-Lys-Pro, Gly-Phe-Leu-Gly; $R_3$ is a peptide chain represented by Ala-Ala-Gin-Thr-Ala-Arg-Gin-His-Pro-Lys-Met-His-Leu-Ala-His-Ser-Thr-Leu or a part thereof, m is 0 or 1, and n is 0 or 1.

* * * * *

UNITED STATES PATENT AND TRADEMARK OFFICE
CERTIFICATE OF CORRECTION

PATENT NO. : 5,142,026
DATED : August 25, 1992
INVENTOR(S) : Iwasa et al

Page 1 of 2

It is certified that error appears in the above-indentified patent and that said Letters Patent is hereby corrected as shown below:

OLD FIGURE 1

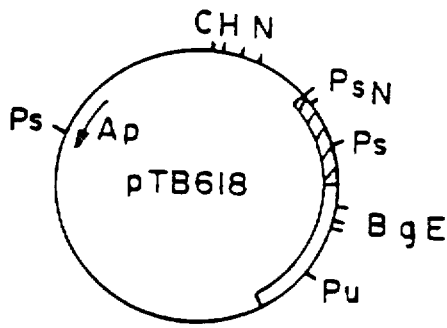

NEW FIGURE 1

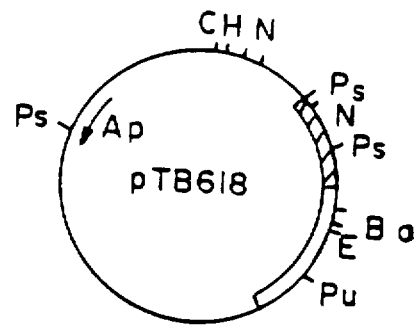

UNITED STATES PATENT AND TRADEMARK OFFICE
CERTIFICATE OF CORRECTION

PATENT NO. : 5,142,026
DATED : August 25, 1992
INVENTOR(S) : Iwasa et al

It is certified that error appears in the above-indentified patent and that said Letters Patent is hereby corrected as shown below:

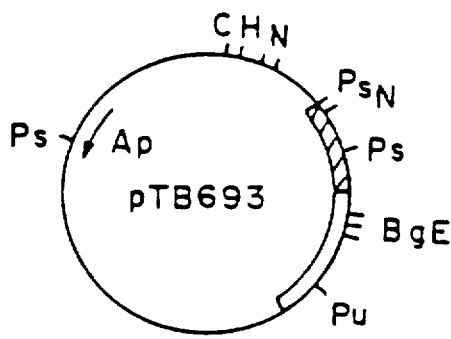 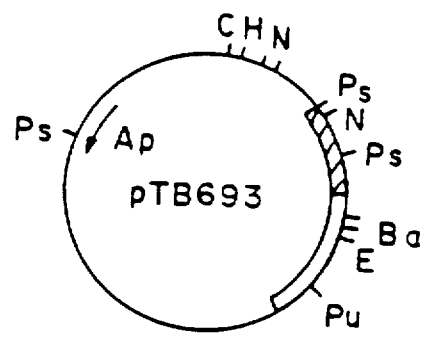

Fig. 4  Add Kb DNA after Isolate 1.2

Fig. 4  Add E47 after E

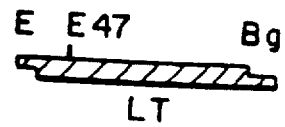

Signed and Sealed this

Fourteenth Day of September, 1993

*Attest:*

BRUCE LEHMAN

*Attesting Officer*    Commissioner of Patents and Trademarks

UNITED STATES PATENT AND TRADEMARK OFFICE
CERTIFICATE OF CORRECTION

PATENT NO. : 5,142,026

DATED : August 25, 1992

INVENTOR(S) : Iwasa et al.

It is certified that error appears in the above-identified patent and that said Letters Patent is hereby corrected as shown below:

Column 26, line 39, change "Gin" to --Gln--.

Column 26, line 35, change "ala" to --Ala--.

Column 26, line 33, change "R" to --$R_1$--.

Signed and Sealed this

First Day of February, 1994

BRUCE LEHMAN

*Attest:*

*Attesting Officer*  *Commissioner of Patents and Trademarks*